United States Patent
Kato et al.

(10) Patent No.: US 10,196,610 B2
(45) Date of Patent: Feb. 5, 2019

(54) ANIMAL CELL CULTURE KIT, METHOD FOR CULTURING ANIMAL CELLS, METHOD FOR SELECTIVE CULTURE OF ANIMAL CELLS AND CELL DIFFERENTIATION METHOD

(75) Inventors: Yukio Kato, Hiroshima (JP); Isao Hirata, Hiroshima (JP); Masami Kanawa, Hiroshima (JP)

(73) Assignee: HIROSHIMA UNIVERSITY, Hiroshima (JP)

( * ) Notice: Subject to any disclaimer, the term of this patent is extended or adjusted under 35 U.S.C. 154(b) by 103 days.

(21) Appl. No.: 14/009,874

(22) PCT Filed: Apr. 4, 2012

(86) PCT No.: PCT/JP2012/059219
§ 371 (c)(1),
(2), (4) Date: Oct. 4, 2013

(87) PCT Pub. No.: WO2012/137830
PCT Pub. Date: Oct. 11, 2012

(65) Prior Publication Data
US 2014/0030804 A1    Jan. 30, 2014

(30) Foreign Application Priority Data
Apr. 5, 2011   (JP) .................. 2011-084119

(51) Int. Cl.
| C12N 5/071 | (2010.01) |
| C12N 5/0775 | (2010.01) |
| C12M 1/00 | (2006.01) |
| C12M 1/12 | (2006.01) |
| C12N 5/00 | (2006.01) |

(52) U.S. Cl.
CPC ........... *C12N 5/0663* (2013.01); *C12M 23/20* (2013.01); *C12M 25/02* (2013.01); *C12N 5/0068* (2013.01); *C12N 2533/20* (2013.01)

(58) Field of Classification Search
None
See application file for complete search history.

(56) References Cited

U.S. PATENT DOCUMENTS

| 2010/0021998 A1 | 1/2010 | Sayal et al. |
| 2010/0167398 A1 | 7/2010 | Sasai et al. |

FOREIGN PATENT DOCUMENTS

| JP | 2009-216483 | 9/2009 |
| JP | 2010-029186 | 2/2010 |
| JP | 2010-166901 | 8/2010 |
| WO | 2006/093207 A1 | 9/2006 |
| WO | 2010/033925 A2 | 3/2010 |

OTHER PUBLICATIONS

Nano and Molecular Electronics Handbook, CRC Press, May 30, 2007, edited by Sergey Edward Lyshevski, pp. 1-6 to 1-8.*
Arima et al. "Effect of wettability and surface functional groups on protein adsorption and cell adhesion using well-defined mixed self-assembled monolayers." ScienceDirect, Biomaterials 28 (2007) 3074-3082.
Couble et al. "Odontoblast Differentiation of Human Dental Pulp Cells in Explant Cultures." Calcif Tissue Int (2000) 66:129-138.
Faucheux et al. "The dependence of fibrillar adhesions in human fibroblasts on substratum chemistry." ScienceDirect, Biomaterials 27 (2006) 234-245.
Fuse et al. "Cell Adhesion and Proliferation Pattens on Mixed Self-assembled Monolayers Carrying Various Ratios of Hydroxyl and Methyl Groups." Dental Materials Journal 26(6): 814-819, 2007.
Igarashi et al. "Selection of Common Markers for Bone Marrow Stromal Cells from Various Bones Using Real-Time RT-PCR: Effects of Passafe Number and Donor Age." Tissue Engineering, vol. 13, No. 10, 2007.
Kubo et al. "Indentification of mesenchymal stem cell (MSC)-transcritpion factors by microarray and knockdown analyses, and signature molecule-marked MSC in bone marrow by immunohistochemistry." Genes to Cells (2009) 14, 407-424.
Roberts et al. "Using Mixed Self-Assembled Monolayers Presenting RGD and (EG)3OH Groups to Characterize Long-Term Attachment of Bovine Capillary Endothelial Cells to Surfaces." J. Am. Chem. Soc. 1998, 120, 6548-6555.
Yokota et al. "Biofunctionality of self-assembled nanolayers composed of cellulosic polymers." Carbohydrate Polymers 74 (2008) 666-672.
Yoshiko et al. "A Subset of Osteoblasts Expressing High Endogenous Levels of PPARy Switches Fate to Adipocytes in the Rat Calvaria Cell Culture Model." PLoS One, Jul. 2010, vol. 5, Issue 7.
Extended European Search Report in co-pending application EP12768652.5 based on PCT/JP2012/059219 dated Dec. 3, 2014.
Derda R et al. "Solid-phase synthesis of alkanethiols for the preparation of self-assembled monolayers," Langmuir 23:11164-11167, 2007.

(Continued)

*Primary Examiner* — Thomas J. Visone
*Assistant Examiner* — Evelyn Y Pyla
(74) *Attorney, Agent, or Firm* — K&L Gates LLP; Louis C. Cullman; David Diamond

(57) ABSTRACT

The invention provides an animal cell culture kit to be used favorably for culturing animal cells, a method for culturing animal cells, a method for culturing selectively animal cells, and a method for differentiating a cell. An animal cell culture kit according to the invention includes an incubator containing one or more types of functional groups selected from the group consisting of hydrophilic functional groups and hydrophobic functional groups at predetermined contents on a surface, and a serum-free culture medium. Since the animal cell culture kit includes an incubator having a functional group suitable for adhesion and proliferation of specific animal cells, proliferation of animal cells can be promoted even with a serum-free culture medium.

3 Claims, 28 Drawing Sheets

(56) References Cited

OTHER PUBLICATIONS

Houseman BT et al. "Efficient solid-phase synthesis of peptide-substituted alkanethiols for the preparation of substrates that support the adhesion of cells," J. Org. Chem. 63:7552-7555, 1998.

Palyvoda O et al. "Culturing neuron cells on electrode with self-assembly monolayer," Biosensors and Bioelectronics 22:2346-2350, 2007.

Barrias, et al. "The correlation between the absorption of adhesive proteins and cell behaviour on hydroxyl-methyl mixed self-absorbed monolayers", Biomaterials, Jan. 2009, vol. 30, No. 3, pp. 307-316.

Notification of Reasons for Rejection dated Feb. 23, 2016 for Japanese Application 2013-508984.

Communication under Article 94(3) issued by European Patent Office dated Jan. 11, 2016 for European Patent Application 12768652.5.

Choi S, Murphy WL. Multifunctional mixed SAMs that promote both cell adhesion and noncovalent DNA Immobilization. Langmuir. 2008;24(13):6873-80.

Inoue S, Imamura M, Umezawa A, Tabata Y. Attachment, proliferation and adipogenic differentiation of adipo-stromal cells on self-assembled monolayers of different chemical compositions. J Biomater Sci Polym Ed. 2008;19(7):893-914.

Curran et al., "Controlling the phenotype and function of mesenchymal cells in vitro by adhesion to silane-modified clean glass surfaces", Biomaterials 26:7057-7067 , (2005).

* cited by examiner

Experiment 1. h-BM MSC in serum free medium(STK2)

Experiment 2. h-BM MSC in serum free medium(STK2)

Experiment 3. h-BM MSC in serum free medium(STK2)

Control

SAM(A6)

SAM(A8)

SAM(A19)

Experiment 1. h-BM MSC in serum free medium(STK2)

SAM(A1)

SAM(A8)

SAM(A14)

SAM(A20)

Experiment 2. h-BM MSC in serum free medium(STK2)

SAM(A1)

SAM(A7)

SAM(A16)

Experiment 3. h-BM MSC in serum free medium(STK2)

FIG. 7
Experiment 4. h-BM MSC in serum free medium(STK2)
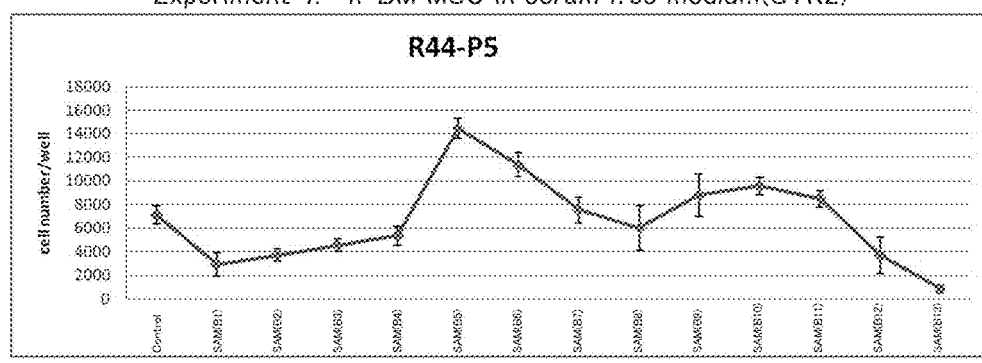
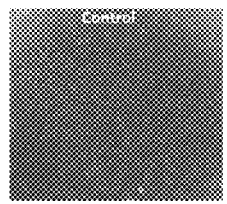   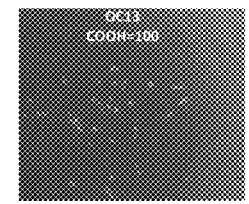
FIG.8A    FIG.8B    FIG.8C    FIG.8D
Control    SAM(B5)    SAM(B8)    SAM(B13)
Experiment 4. h-BM MSC in serum free medium(STK2)

FIG.9A
Experiment 5. h-BM MSC in 10%FBS
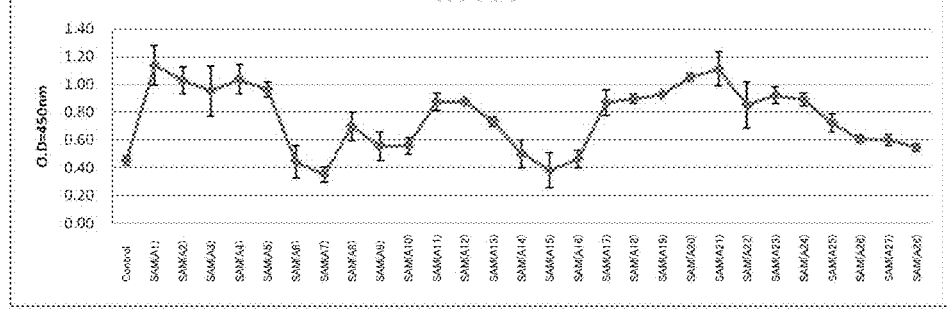
FIG.9B
Experiment 6. h-BM MSC in 10%FBS
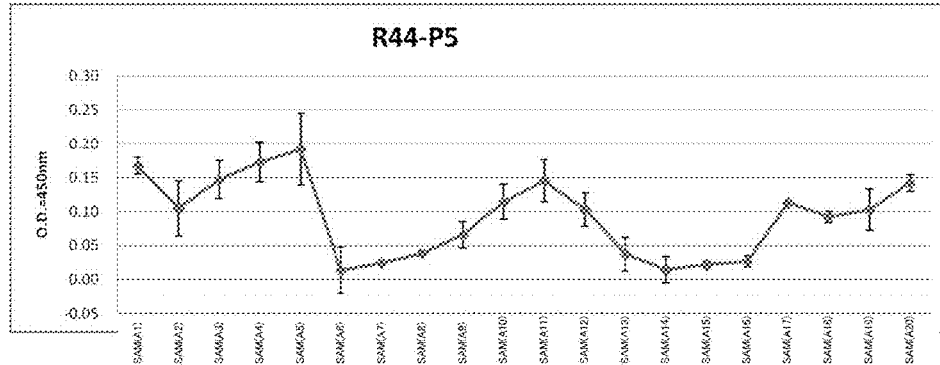
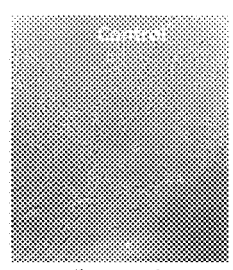
Control
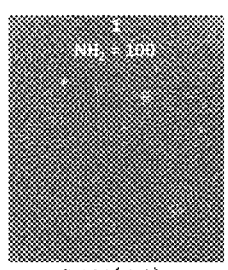
SAM(A1)
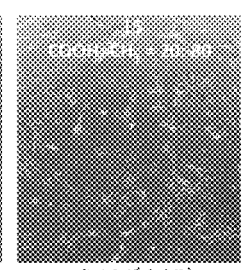
SAM(A15)
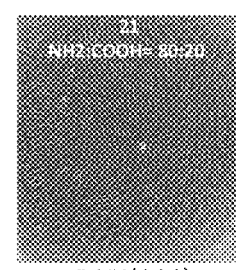
SAM(A21)
FIG.10A  FIG.10B  FIG.10C  FIG.10D
Experiment 5. h-BM MSC in 10%FBS Experiment 1. h-BM MSC in serum free medium(STK2)

Experiment 5. h-BM MSC in 10%FBS

Experiment 11-1. rat-primary MSC in serum free medium (STK1)

Experiment 11-2. rat-primary MSC in serum free medium (STK1)

Experiment 12. rat-primary MSC in DMEM+10%FBS

Experiment 13. rat-primary MSC in αMEM+10%FBS

Control

SAM(A6)

SAM(A11)

SAM(A15)

SAM(A25)

Experiment 11-1. rat-primary MSC in serum free medium (STK1)

Control

SAM(A4)

SAM(A11)

SAM(A18)

SAM(A25)

Experiment 11-2. rat-primary MSC in serum free medium (STK1)

Control    SAM(A14)   SAM(A17)   SAM(A25)

Experiment 12. rat-primary MSC in DMEM+10%FBS

Control    SAM(A6)    SAM(A9)

SAM(A11)   SAM(A19)   SAM(A28)

Experiment 13. rat-primary MSC in αMEM+10%FBS

Experiment 21. h-synovial MSC(S6-P2) in serum free medium (STK2)

Experiment 22. h-synovial MSC in serum free medium (STK1)

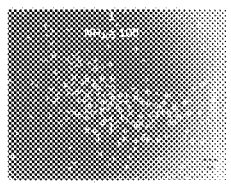 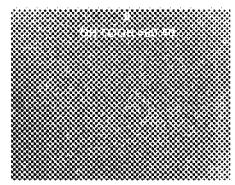 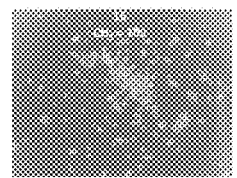 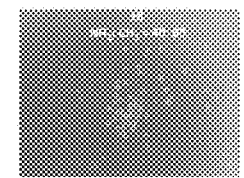
FIG.20A  FIG.20B  FIG.20C  FIG.20D
SAM(A1)   SAM(A8)   SAM(A16)   SAM(A18)
Experiment 21. h-synovial MSC(S6-P2) in serum free medium (STK2)
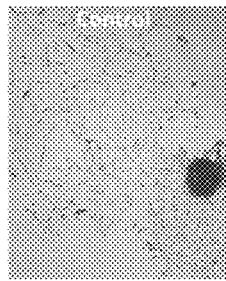 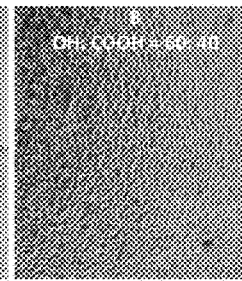 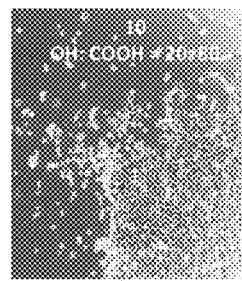 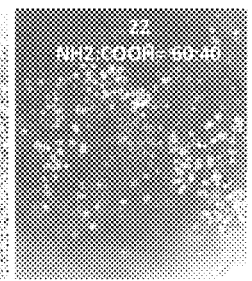
FIG.21A  FIG.21B  FIG.21C  FIG.21D
Control   SAM(A8)   SAM(A10)   SAM(A22)
Experiment 22. h-synovial MSC in serum free medium (STK1)

FIG.22
Experiment 23. h-Dental pulp MSC in serum free medium (STK2)
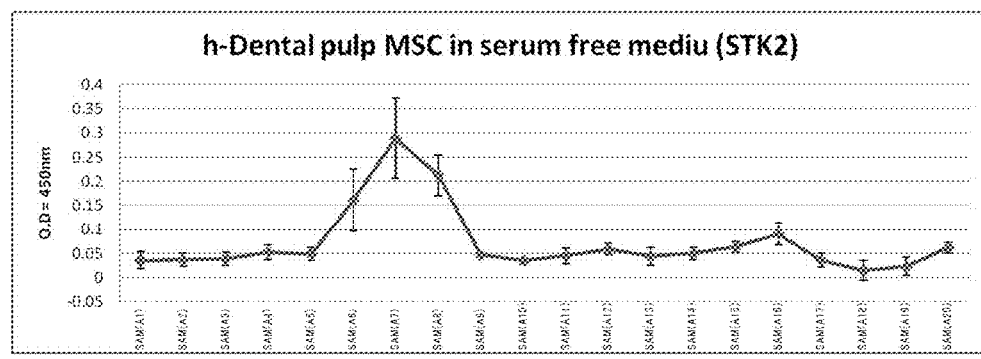
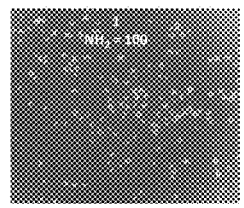 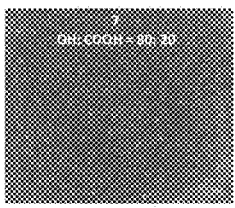 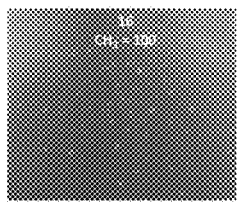 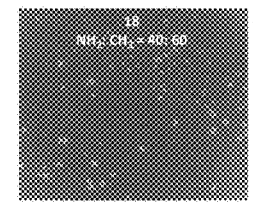
FIG.23A    FIG.23B    FIG.23C    FIG.23D
SAM(A1)    SAM(A7)    SAM(A16)    SAM(A18)
Experiment 23. h-Dental pulp MSC in serum free medium (STK2)

FIG.24A
Experiment 31. Fibroblast(1429-P8) in serum free medium (STK2)
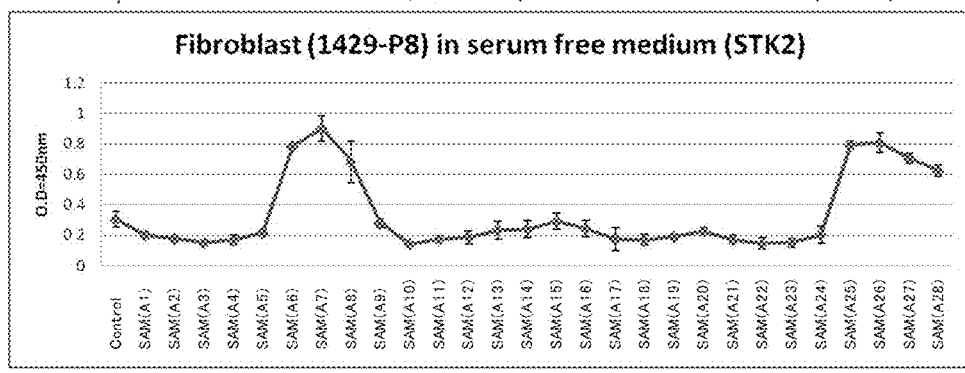
FIG.24B
Experiment 32. Fibroblast(1429-P8) in 10%FBS
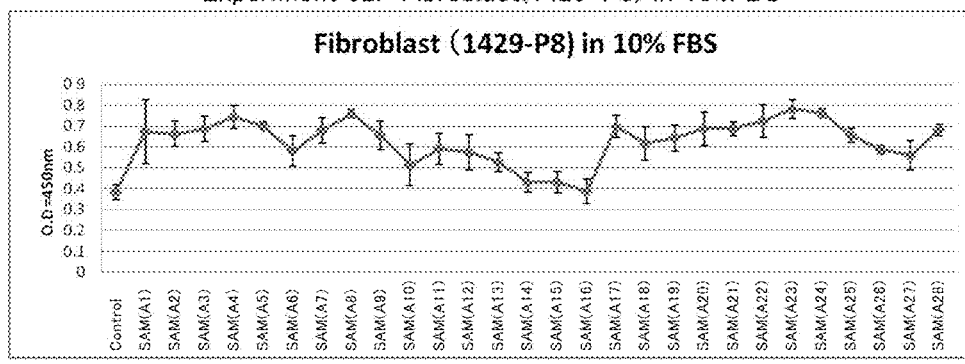
| FIG.25A | FIG.25B | FIG.25C | FIG.25D |
|---|---|---|---|
| 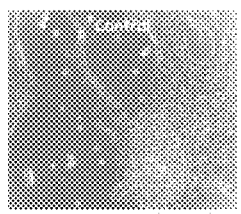 | 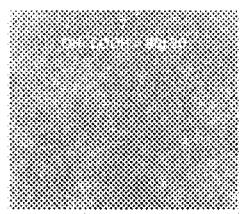 | 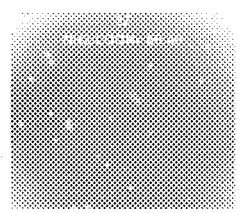 | 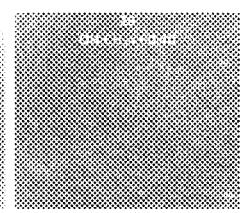 |
| Control | SAM(A7) | SAM(A22) | SAM(A26) |
Experiment 31. Fibroblast(1429-P8) in serum free medium (STK2)

FIG.26
Experiment 33. rat-Osteoblasts (P1) in serum free medium (STK2)
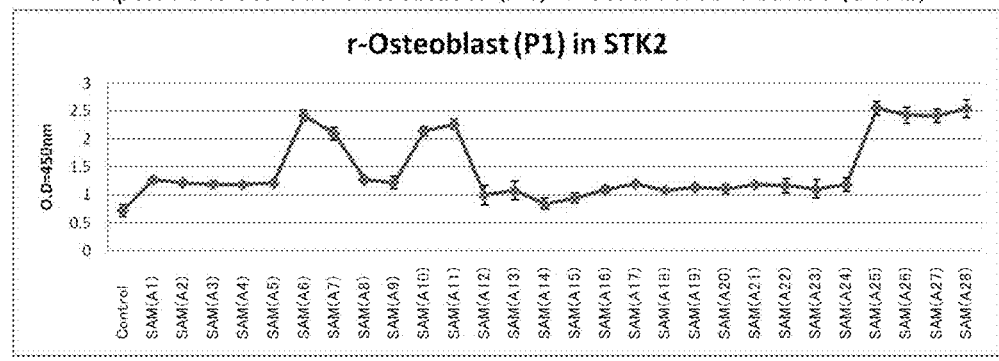
FIG.27A    FIG.27B    FIG.27C    FIG.27D
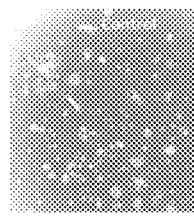 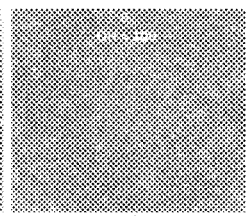 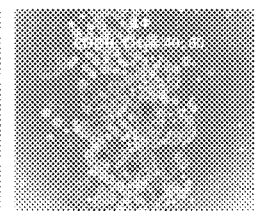 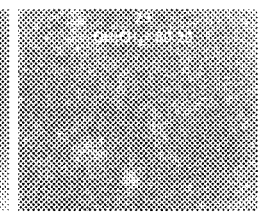
Control      SAM(A6)      SAM(A14)      SAM(A25)
Experiment 33. rat-Osteoblasts (P1) in serum free medium (STK2)

Experiment 41. rat-BM MSC (P3) in serum free medium (STK2)

Experiment 42. rat-BM MSC (P3) in 10%FBS

Experiment 41. rat-BM MSC (P3) in serum free medium(STK2)

Experiment 42. rat-BM MSC (P3) in 10%FBS

FIG.30A
Control
FIG.30B
SAM(A6)
FIG.30C
SAM(A11)
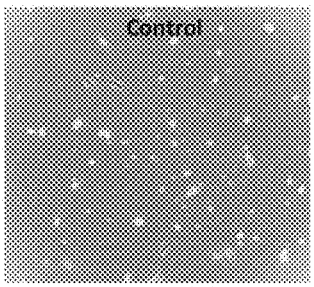
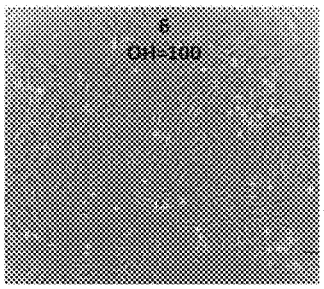
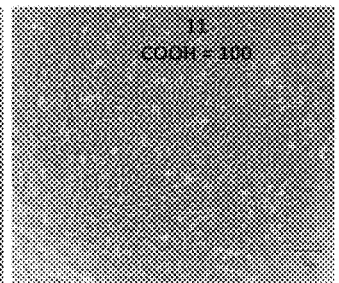
FIG.30D
SAM(A14)
FIG.30E
SAM(A25)
FIG.30F
SAM(A28)
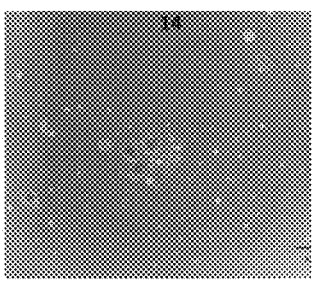
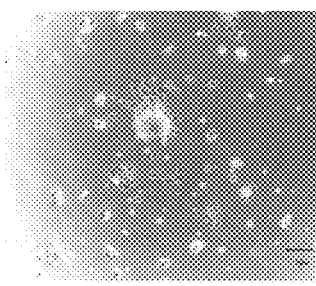
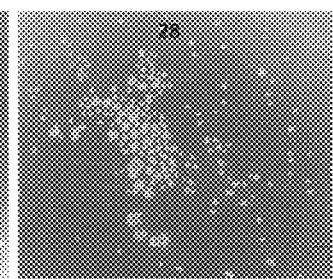
Experiment 41. rat-BM MSC (P3) in serum free medium (STK2)

Control

SAM(A7)

SAM(A11)

SAM(A16)

SAM(A24)

SAM(A28)

Experiment 42. rat-BM MSC (P3) in 10%FBS

Experiment 51. h-primary MSC (R82) in serum free medium (STK1)

Control      SAM(A7)      SAM(A8)

Experiment 51. h-primary MSC (R82) in serum free medium (STK1)

Experiment 52. h-primary MSC (R83) in serum free medium (STK1)

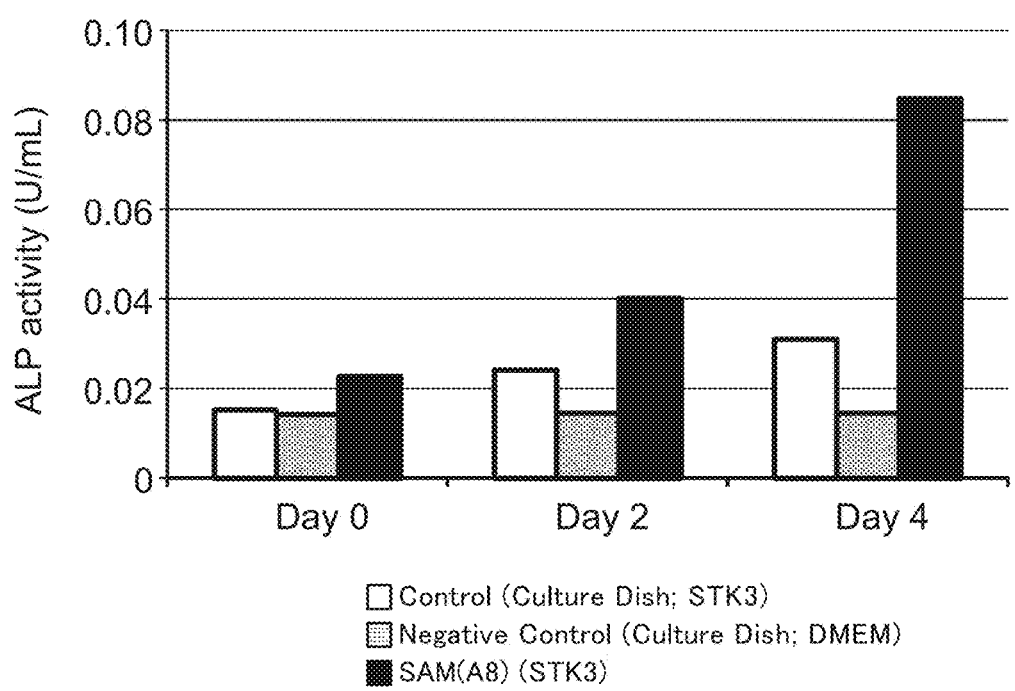

ANIMAL CELL CULTURE KIT, METHOD FOR CULTURING ANIMAL CELLS, METHOD FOR SELECTIVE CULTURE OF ANIMAL CELLS AND CELL DIFFERENTIATION METHOD

CROSS REFERENCE TO RELATED APPLICATIONS

The present application is a national phase of PCT/JP2012/059219 filed on Apr. 4, 2012, which claims priority to Japanese Patent Application B 2011-084119 filed on Apr. 5, 2011, the entire disclosures of which are incorporated by reference herein.

TECHNICAL FIELD

The present invention relates to an animal cell culture kit, a method for culturing animal cells, a method for culturing selectively animal cells, and a method for differentiating a cell.

BACKGROUND ART

For culturing animal cells, a polystyrene culture dish for tissue culture, to which various ionic groups are introduced by plasma irradiation or the like, has been broadly used. The degree of ionization by introduction of ionic groups is, however, not invariable, and the surface composition is not defined chemically. Nevertheless, even with such an ordinary polystyrene culture dish for tissue culture, an immortalized cell line can proliferate well in many cases.

On the other hand, since primary animal cells isolated from tissues constitute heterogeneous cell populations, they have not been habituated to a cultivation system and their proliferation rates are low in many cases. As the result, when a polystyrene culture dish for tissue culture is used, a basic research, and development of regenerative medicine and a biopharmaceutical using animal cells are difficult. Further, with a polystyrene culture dish for tissue culture, even when a proliferation factor or a cytokine is added, a target cell can be hardly proliferated selectively. Further, a contamination cell other than a target cell cannot be removed from a heterogeneous cell population. Consequently, a research and development of regenerative medicine or a biopharmaceutical is difficult.

To overcome the drawback of an ordinary polystyrene culture dish for tissue culture, as a coating material an adhesion factor, such as fibronectin and collagen, a partial peptide of an adhesion factor, polylysine and an extracellular matrix such as a basement membrane are used. Such coating materials are however expensive, and the effect on culture has been restricted to limited cells.

Meanwhile, for a culture of animal cells, a serum-containing culture medium, to which a high concentration of serum is added, is generally used. However, since serum is a natural ingredient, a serum-containing culture medium has drawbacks of uncertain composition, lot-to-lot variance, a risk of contamination of a pathogenic microbe, and a risk of an immunoreaction. Therefore in using a serum-containing culture medium, variance in cell proliferation (differentiation) is apt to appear. For overcoming the drawbacks, development of a serum-free culture medium is underway. However, since a serum-free culture medium does not contain an adhesion factor of serum, when culture in an ordinary polystyrene culture dish for tissue culture is attempted, there is a drawback in that adhesion and proliferation of a cell becomes difficult.

Further, although a plastic culture dish, to which $NH_2$ group, or COOH group is added, is on the market recent years, the influence on cell proliferation has not been clarified thoroughly yet. Meanwhile, a culture dish provided with a self-assembled monolayer (SAM) on the culture dish surface has been investigated in some studies. Changing a combination of 3 types of functional groups ($CH_3/OH$, $CH_3/COOH$, $CH_3/NH_2$) composing an SAM and their contents, influence on adhesion of a cancer cell and an established (immortalized) cell line was investigated in the presence of a 2 to 10% fetal bovine serum (Non Patent Literature 1).

Further, influence of a combination of 2 types of functional groups on a short term proliferation of a cancer cell and an established (immortalized) cell line has been investigated (Non Patent Literature 2).

Adhesion of a vascular endothelial cell to SAM with an RGD peptide has been reported (Non Patent Literature 3).

CITATION LIST

Non Patent Literature

Non Patent Literature 1: Arima Y, Iwata H., Biomaterials, 28: 3074-3082, 2007.

Non Patent Literature 2: Fuse Y, Hirata I, Kurihara H, Okazaki M, "Cell adhesion and proliferation patterns on mixed self-assembled monolayers carrying various ratios of hydroxyl and methyl groups.", Dent Mater J., 2007, 26(6): 814-819.

Non Patent Literature 3: J Am Chem Soc, 1998, 120: 6548-6555.

SUMMARY OF INVENTION

Technical Problem

However, Non Patent Literature 1 and Non Patent Literature 2 do not mention addition of a functional group for promoting proliferation beyond the level of an ordinary polystyrene culture dish for tissue culture, or a cell other than an immortalize cell line (primary cell, stem cell, or the like). Existence of a functional group which suppresses extremely cell adhesion is within expectation. Meanwhile, with respect to Non Patent Literature 3 there is no surprise at promotion of cell adhesion by an RGD peptide. In other words, although heretofore there have been basic studies concerning addition of functional groups which have influence on cell adhesion, there have been no industrial idea or study, nor an experimental result that higher level cell proliferation is to be seeked by an SAM added with a functional group compared to an ordinary culture dish.

Further, serum was used in the past studies involving an SAM, however, a serum protein adheres to the SAM and interferes in interaction with a cell. Therefore a formulation with a functional group for an incubator surface could not be optimized with chemically defined specifications.

The present invention was conducted under such circumstances with an object to provide an animal cell culture kit to be used favorably for culturing animal cells, a method for culturing animal cells, a method for culturing selectively animal cells, and a method for differentiating a cell.

Solution to Problem

An animal cell culture kit according to the first aspect of the present invention comprises an incubator comprising one or more types of functional groups selected from the group consisting of hydrophilic functional groups and hydrophobic functional groups at predetermined contents on a surface, and a serum-free culture medium.

The incubator may be provided with a self-assembled monolayer comprising the functional group at a predetermined content on a surface.

The hydrophilic functional group is preferably hydroxyl group, amino group or carboxyl group, and the hydrophobic functional group is preferably an alkyl group.

The incubator may be in a mode comprising hydroxyl group:carboxyl group at a content ratio from 100:0 to 20:80, and promoting adhesion and proliferation of a human bone marrow mesenchymal stem cell.

Further it may be in a mode comprising amino group: hydroxyl group at a content ratio of 40:60, carboxyl group: methyl group from 100:0 to 80:20, amino group:methyl group from 20:80 to 80:20, amino group:carboxyl group from 40:60 to 20:80, or hydroxyl group:methyl group from 100:0 to 80:20, and promoting adhesion and proliferation of a primary rat mesenchymal stem cell in a heterogeneous cell population.

Further it may be in a mode comprising hydroxyl group: carboxyl group at a content ratio from 100:0 to 40:60, and promoting adhesion and proliferation of a mesenchymal stem cell derived from a human synovial membrane.

Further it may be in a mode comprising hydroxyl group: carboxyl group at a content ratio from 100:0 to 60:40, and promoting adhesion and proliferation of a mesenchymal stem cell derived from a human dental pulp.

Further it may be in a mode comprising hydroxyl group: carboxyl group at a content ratio from 100:0 to 40:60, or hydroxyl group:methyl group from 80:20 to 20:80, and promoting adhesion and proliferation of a human fibroblast.

Further it may be in a mode comprising hydroxyl group: carboxyl group at a content ratio from 100:0 to 0:100, or hydroxyl group:methyl group from 80:20 to 20:80, and promoting adhesion and proliferation of a rat osteoblast.

Further it may be in a mode comprising hydroxyl group: carboxyl group at a content ratio from 100:0 to 0:100, or carboxyl group:methyl group from 100:0 to 80:20, and promoting adhesion and proliferation of a rat bone marrow mesenchymal stem cell.

Further it may be in a mode comprising hydroxyl group: carboxyl group at a content ratio from 100:0 to 40:60, and promoting adhesion and proliferation of a human primary mesenchymal stem cell.

Further it may be in a mode comprising hydroxyl group: carboxyl group at a content ratio from 100:0 to 40:60, and promoting adhesion and proliferation of a human mesenchymal stem cell.

A method for culturing animal cells according to the second aspect of the present invention promotes adhesion and proliferation of a predetermined animal cell using an incubator comprising one or more types of functional groups selected from the group consisting of hydrophilic functional groups and hydrophobic functional groups at predetermined contents on a surface, and a serum-free culture medium.

A method for culturing selectively animal cells according to the third aspect of the present invention promotes adhesion and proliferation of a predetermined animal cell selectively out of a heterogeneous cell population using an incubator comprising one or more types of functional groups selected from the group consisting of hydrophilic functional groups and hydrophobic functional groups at predetermined contents on a surface, and a serum-free culture medium.

A method for culturing animal cells according to the fourth aspect of the present invention promotes proliferation of a human mesenchymal stem cell, a human fibroblast, or a rat mesenchymal stem cell using a serum-containing culture medium and an incubator comprising amino group: hydroxyl group at a content ratio from 100:0 to 20:80, hydroxyl group:carboxyl group from 80:20 to 20:80, carboxyl group:methyl group from 100:0 to 60:40, amino group:methyl group from 80:20 to 20:80, or amino group: carboxyl group from 80:20 to 20:80 on a surface.

A method for differentiating a cell according to the fifth aspect of the present invention differentiates a human bone marrow mesenchymal stem cell to chondrocyte or osteocyte by culturing the human bone marrow mesenchymal stem cell using an incubator comprising one or more types of functional groups selected from the group consisting of hydrophilic functional groups and hydrophobic functional groups at predetermined contents on a surface, and a serum-free differentiation-inducing culture medium.

Further, by the method the human bone marrow mesenchymal stem cell may be differentiated to chondrocyte using the incubator comprising hydroxyl group:carboxyl group at a content ratio from 100:0 to 20:80 and a serum-free cartilage differentiation-inducing culture medium.

Further, by the method the human bone marrow mesenchymal stem cell may be differentiated to osteocyte using the incubator comprising hydroxyl group:carboxyl group at a content ratio from 100:0 to 20:80 and a serum-free osteogenic differentiation-inducing culture medium.

A method for differentiating a cell according to the sixth aspect of the present invention, differentiates a human bone marrow mesenchymal stem cell to adipocyte by culturing the bone marrow mesenchymal stem cell using an incubator comprising one or more types of functional groups selected from the group consisting of hydrophilic functional groups and hydrophobic functional groups at predetermined contents on a surface, and an adipose differentiation-inducing culture medium.

Advantageous Effects of Invention

Since an animal cell culture kit according to the present invention includes an incubator having functional groups suitable for adhesion and proliferation of a specific animal cell, proliferation of animal cells can be promoted even with a serum-free culture medium.

BRIEF DESCRIPTION OF DRAWINGS

FIG. 2: with respect to Examples.

FIG. 4 is photographs of cells after 4-day culture in Experiment 1, wherein

FIG. 5 is photographs of cells after 4-day culture in Experiment 2, wherein

FIG. 6 is photographs of cells after 4-day culture in Experiment 3, wherein

FIG. 7 is a diagram showing the results of cell number measurements after 4-day culture in Experiment 4;

FIG. 8 is photographs of cells after 4-day culture in Experiment 4, wherein FIG. 8A is a photograph of a control, FIG. 8B is of SAM (B5), FIG. 8C is of SAM (B8), and FIG. 8D is of SAM (B13);

FIG. 9A is a diagram showing the results of MTT assays after 4-day culture in Experiment 5, and FIG. 9B is a diagram showing the results of MTT assays after 4-day culture in Experiment 6;

FIG. 10 is photographs of cells after 4-day culture in Experiment 5, wherein FIG. 10A is a photograph of a control, FIG. 10B is of SAM (A1), FIG. 10C is of SAM (A15), and FIG. 10D is of SAM (A21);

FIG. 15 is photographs of cells after 7-day culture in Experiment 11-1, wherein

FIG. 16 is photographs of cells after 8-day culture in Experiment 11-2, wherein

FIG. 17 is photographs of cells after 8-day culture in Experiment 12, wherein

FIG. 18 is photographs of cells after 7-day culture in Experiment 13, wherein

FIG. 20 is photographs of cells after 4-day culture in Experiment 21, wherein FIG. 20A is a photograph of SAM (A1), FIG. 20B is of SAM (A8), FIG. 20C is of SAM (A16), and FIG. 20D is of SAM (A18);

FIG. 21 is photographs of cells after 14-day culture in Experiment 22, wherein FIG. 21A is a photograph of a control, FIG. 21B is of SAM (A8), FIG. 21C is of SAM (A10), and FIG. 21D is of SAM (A22);

FIG. 22 is a diagram showing the results of MTT assays after 4-day culture in Experiment 23;

FIG. 23 is photographs of cells after 4-day culture in Experiment 23, wherein FIG. 23A is a photograph of SAM (A1), FIG. 23B is of SAM (A7), FIG. 23C is of SAM (A16), and FIG. 23D is of SAM (A18);

FIG. 24A is a diagram showing the results of MTT assays after 4-day culture in Experiment 31, and FIG. 24B is a diagram showing the results of MTT assays after 4-day culture in Experiment 32;

FIG. 25 is photographs of cells after 4-day culture in Experiment 31, wherein FIG. 25A is a photograph of a control, FIG. 25B is of SAM (A7), FIG. 25C is of SAM (A22), and FIG. 25D is of SAM (A26);

FIG. 26 is a diagram showing the results of MTT assays after 4-day culture in Experiment 33;

FIG. 27 is photographs of cells after 4-day culture in Experiment 33, wherein FIG. 27A is a photograph of a control, FIG. 27B is of SAM (A6), FIG. 27C is of SAM (A14), and FIG. 27D is of SAM (A25);

FIG. 30 is photographs of cells after 4-day culture in Experiment 41, wherein FIG. 30A is a photograph of a control, FIG. 30B is of SAM (A6), FIG. 30C is of SAM (A11), FIG. 30D is of SAM (A14), FIG. 30E is of SAM (A25), and FIG. 30F is of SAM (A28);

FIG. 31 is photographs of cells after 4-day culture in Experiment 42, wherein

FIG. 33 is photographs of cells after 14-day culture in Experiment 51, wherein

FIG. 35 is photographs of cells cultured with SAM (A1) in Experiment 61, wherein

FIG. 36 is photographs of cells cultured with SAM (A6) in Experiment 62, wherein

FIG. 37 is photographs of cells cultured with SAM (A8) in Experiment 63, wherein

FIG. 38 is photographs of cells cultured with SAM (A11) in Experiment 64, wherein

FIG. 45 is a graph showing the measurement results of ALP activity.

DESCRIPTION OF EMBODIMENTS

An animal cell culture kit, a method for culturing animal cells, a method for culturing selectively animal cells, and a method for differentiating a cell according to the present embodiment will be described below. The animal cell culture kit according to the present embodiment is composed of an incubator and a serum-free culture medium.

An incubator contains one or more types of functional groups selected from the group consisting of hydrophilic functional groups and hydrophobic functional groups at predetermined contents on a surface. More specifically, an incubator has a self-assembled monolayer (hereinafter referred to as "SAM") on a surface. An SAM is a form, in which one or more types of functional groups out of the group consisting of hydrophilic functional groups and hydrophobic functional groups are exposed to a surface at predetermined contents. In this case, an SAM may contain two or more different types of hydrophilic functional groups or hydrophobic functional groups, or contain both. Examples of a hydrophilic functional group include hydroxyl group, amino group, carboxyl group, and a nitro group, and examples of a hydrophobic functional group include alkyl group, such as methyl group, ethyl group, and propyl group, phenyl group, cyclohexyl group, cyclopentyl group, and fluoro group. A hydrophilic functional group may be either of a positive charge functional group and a negative charge functional group, for example, amino group may be in a form of $NH_3^+$ with a proton, and carboxyl group may be in a form of $COO^-$ by deprotonation.

Figure 1A:
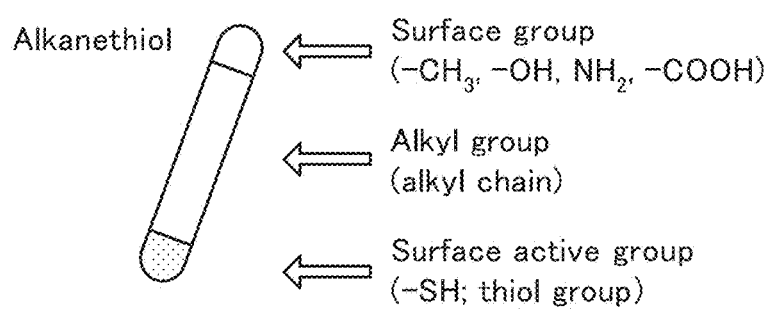
FIG. 1A is a schematic diagram of an alkanethiol.

An SAM can be produced as follows. Dissolving an alkanethiol in a solvent such as ethanol to prepare an alkanethiol solution. As depicted in a schematic diagram in FIG. 1A, an alkanethiol has at an end of a linear alkyl chain a thiol group (—SH), and at the other end methyl group (—CH$_3$), hydroxyl group (—OH), amino group (—NH$_2$) or carboxyl group (—COOH). Although there is no particular restriction on the carbon number of an alkyl chain, it is from 5 to 20.

Figure 1B:
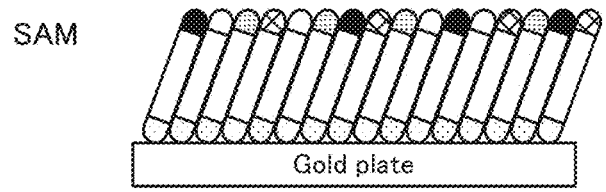
FIG. 1B is a schematic diagram of an SAM.

By dipping a gold-deposited substrate or the like into a prepared alkanethiol solution, or otherwise, an alkanethiol is bonded to a gold-deposited substrate. As depicted schematically in FIG. 1B, an SAM is formed on a gold-deposited substrate. Since a thiol group on an alkanethiol bonds specifically to gold and the molecules form a high density, highly oriented structure due to van der Waals forces between alkyl chains, a monolayer with functional groups exposed to surfaces is formed on a gold-deposited substrate. By providing a polystyrene culture dish or the like with such a gold-deposited substrate, an incubator can be obtained. Alternatively, using a gold-modified culture dish or the like, an alkanethiol may be bonded directly.

By preparing an alkanethiol solution using any single or plural types in a combination out of the above alkanethiols, SAMs with various functional groups on a surface can be obtained. The surface composition of an SAM becomes almost the same as the composition of an alkanethiol solution used. Therefore by forming an SAM through preparation of an alkanethiol solution by dissolving alkanethiols having the 4 types of functional groups at predetermined contents depending on animal cells to be proliferated, an incubator suitable for proliferation of the animal cell can be obtained.

A serum-free culture medium is a culture medium not containing serum and has few unidentified factors. Consequently, it has advantages that constant performance can be obtained compared to a serum-containing culture medium, purification out of the culture medium as well as processing thereafter are easy, accurate evaluation of a cellular function is easy, and regulation of physiological reactivity is easy.

On the other hand, since a serum-free culture medium does not contain serum, there exists substantially no adhesion factor of serum (substrate adhesion cell). Conceivably in the process of cell proliferation, firstly an adhesion factor adheres to a culture dish or the like, to which a cell adheres through the adhesion factor and proliferates. Since there is almost no adhesion factor in a serum-free culture medium, adhesion and proliferation of a cell can hardly take place.

However, an animal cell culture kit according to the present embodiment includes an incubator having an SAM of a mode with various functional groups exposed at a predetermined ratio, and the surface composition of an incubator can be adjusted to a surface composition suitable for adhesion, extension, and proliferation of a predetermined animal cell. Therefore, even with a serum-free culture medium, adhesion, extension, and proliferation of a predetermined animal cell can be promoted. Further, with respect to a stem cell such as a mesenchymal stem cell capable of differentiating to cells of a plurality of lineages, cell differentiation can be also promoted.

As a serum-free culture medium, generally used basic culture media such as isosmotic pH-balanced solutions mixed with salts, amino acids, saccharides, vitamins and other essential trace nutrients, may be used in a combination, and a culture medium composed of a basic culture medium and various additives may be also used. Examples of an appropriate serum-free culture medium include STK1 (trade name), STK2 (trade name), and STK3 (trade name) (all produced by DS Pharma Biomedical Co., Ltd.).

From the above, with the animal cell culture kit, selective adhesion and proliferation of a specific target animal cell out of a heterogeneous cell population (for example, a cell population in a bone marrow fluid) is possible by combining an SAM suitable for adhesion and proliferation of the specific animal cell and a serum-free culture medium.

Although an incubator provided with a culture dish, for which an SAM is formed on a gold-deposited substrate, is described above, a substrate, on which an SAM is formed using a gold foil or a gold colloid instead of a gold-deposited substrate, may be used, and also a substrate with a metal other than gold such as aluminum, titanium, platinum, and silver, or the like may be used. Further, a substrate of a ceramic, such as an inorganic metallic oxide, including aluminum oxide, silicon oxide, titanium oxide or the like, and a glass, on which an SAM is formed, may be used.

Further, it is also possible that the substrate is processed to the shape of a culture dish, an SAM is formed on a surface thereof, and the obtained substrate with the formed SAM is laminated on a culture dish to obtain an incubator.

Further, an incubator with a culture dish, on which surface an SAM is directly formed, while the culture dish is in a form that a culture dish itself is composed of the above materials, or the culture dish surface is modified with the above materials, instead of being provided with a substrate such as a gold-deposited substrate, may be also used.

Although as an incubator an example of a culture dish is described above, it is not limited to a culture dish insofar as it is usable for culture of animal cells. Further it may be in a mode that the functional groups are directly attached to a surface without forming an SAM using alkanethiols. For example it may be in a mode that the functional groups are attached to a surface of a biomaterial for implantation or the like. Further it may be also in a mode that the functional groups are directly attached to glass or the like by a silane coupling method, to titanium by surface processing, or to various biomaterial polymers or the like.

Various SAM compositions suitable for proliferation of animal cells will be described below based on Examples.

EXAMPLES

Influence of a surface composition of an SAM acting on adhesion and proliferation of animal cells was tested, by preparing SAMs with various surface compositions, and combining the same with various animal cells and culture media.

(Preparation of SAM)

Firstly, an SAM was prepared on a gold-deposited substrate as follows.

As 1-dodecanethiol (hereinafter described as "$CH_3$—SH") a product of Wako Pure Chemical Industries, Ltd. was used. As 11-mercapto-1-undecanol (hereinafter described as "OH—SH"), 11-mercapto-1-undecanoic acid (hereinafter described as "COOH—SH"), and 11-amino-1-undecanethiol (hereinafter described as "$NH_2$—SH") products of Sigma-Aldrich, Inc. were used.

Surfaces of a gold-deposited substrate were washed with a Piranha solution (concentrated sulfuric acid:30% hydrogen peroxide water=7:3). Alkanethiol solutions were prepared by dissolving alkanethiols ($CH_3$—SH, OH—SH, COOH—SH, and $NH_2$—SH) in ethanol deoxidized with a nitrogen gas according to various combinations and ratios set forth in Table 1 to 1 mmol/L totally.

TABLE 1

|  | $NH_2$ | OH | COOH | $CH_3$ |
|---|---|---|---|---|
| SAM(A1) | 100 | | | |
| SAM(A2) | 80 | 20 | | |
| SAM(A3) | 60 | 40 | | |
| SAM(A4) | 40 | 60 | | |
| SAM(A5) | 20 | 80 | | |
| SAM(A6) | | 100 | | |
| SAM(A7) | | 80 | 20 | |
| SAM(A8) | | 60 | 40 | |
| SAM(A9) | | 40 | 60 | |
| SAM(A10) | | 20 | 80 | |
| SAM(A11) | | | 100 | |
| SAM(A12) | | | 80 | 20 |

TABLE 1-continued

|  | $NH_2$ | OH | COOH | $CH_3$ |
|---|---|---|---|---|
| SAM(A13) | | | 60 | 40 |
| SAM(A14) | | | 40 | 60 |
| SAM(A15) | | | 20 | 80 |
| SAM(A16) | | | | 100 |
| SAM(A17) | 20 | | | 80 |
| SAM(A18) | 40 | | | 60 |
| SAM(A19) | 60 | | | 40 |
| SAM(A20) | 80 | | | 20 |
| SAM(A21) | 80 | 20 | | |
| SAM(A22) | 60 | 40 | | |
| SAM(A23) | 40 | 60 | | |
| SAM(A24) | 20 | 80 | | |
| SAM(A25) | | 80 | | 20 |
| SAM(A26) | | 60 | | 40 |
| SAM(A27) | | 40 | | 60 |
| SAM(A28) | | 20 | | 80 |

A gold-deposited substrate was immersed in a prepared alkanethiol solution for 24 hours to produce one of various SAMs (hereinafter described respectively as "SAM (A1) up to SAM (A28)") on a gold-deposited substrate. The produced SAMs were preserved in 2-propanol before use for an experiment.

(Analysis of SAM Surface Composition)

The surface elementary compositions of the produced SAM (A1) to (A20) were determined by X-ray photoelectron spectroscopy (XPS AXIS-HS, by Kratos Analytical Limited, Manchester, UK). Measurements were carried out at a pressure of $10^{-7}$ Pa or less. A sample surface was irradiated with A11-Kapha monochromatic X-ray under conditions of acceleration voltage at 15 kV, and filament current at 10 mA, and relative element contents of carbon and oxygen were measured under condition of a photoelectron detachment angle at 90° C.

Figure 2A:
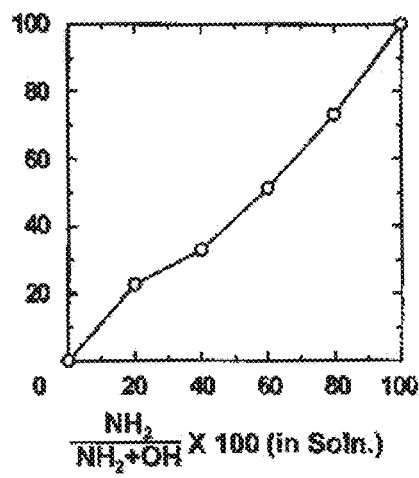
FIG. 2A is a graph showing a content ratio of functional groups in a prepared SAM surface to an addition ratio of alkanethiols ($NH_2$—SH and OH—SH)
Figure 2B:
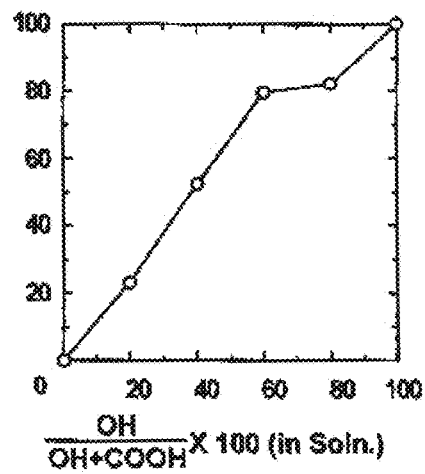
FIG. 2B is a graph showing a content ratio of functional groups on a prepared SAM surface to addition ratios of alkanethiols (OH—SH and COOH—SH)
Figure 2C:
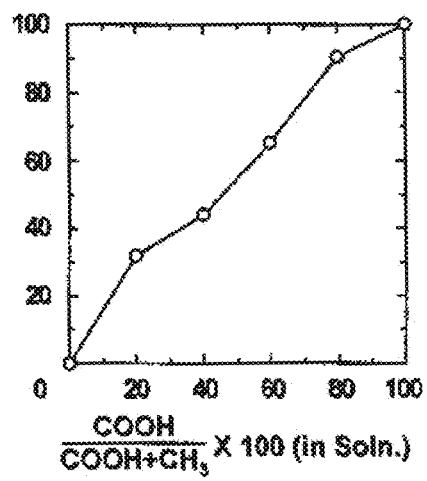
FIG. 2C is a graph showing a content ratio of functional groups on a prepared SAM surface to addition ratios of alkanethiols (COOH—SH and $CH_3$—SH)
Figure 2D:
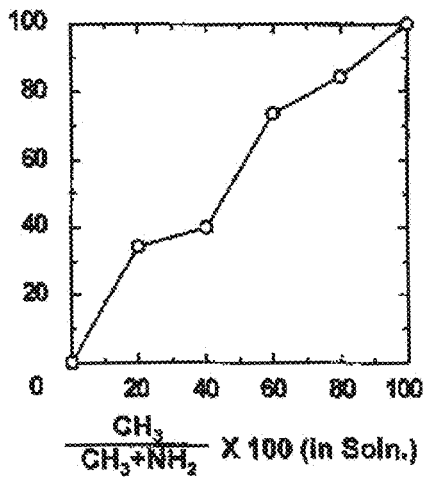
FIG. 2D is a graph showing a content ratio of functional groups on a prepared SAM surface to addition ratios of alkanethiols ($CH_3$—SH and $NH_2$—SH)

FIG. 2A shows the relative content of a functional group on a surface of a prepared SAM to the relative content of $NH_2$—SH and OH—SH in an alkanethiol solution, FIG. 2B shows the relative content of a functional group on a surface of a prepared SAM to the relative content of OH—SH and COOH—SH in an alkanethiol solution, FIG. 2C shows the relative content of a functional group on a surface of a prepared SAM to the relative content of COOH—SH and $CH_3$—SH in an alkanethiol solution, and FIG. 2D shows the relative content of a functional group on a surface of a prepared SAM to the relative content of $CH_3$—SH and $NH_2$—SH in an alkanethiol solution, respectively.

As obvious from FIG. 2A, if the relative content of amino group with respect to hydroxyl group in an alkanethiol solution becomes higher, an SAM having the outermost surface layer with a higher relative content of amino group with respect to hydroxyl group is obtained. As seen from FIG. 2B, FIG. 2C, and FIG. 2D, in the cases alkanethiol solutions having other functional groups at the end, the trends are identical. Accordingly, it is known that the composition of functional groups on an SAM surface can be regulated according to a mixture ratio of alkanethiols.

Using the SAMs prepared as above, animal cells were cultured in the following tests.

In some experiments, alkanethiol solutions were prepared according to the mixture ratios shown in Table 2 and various SAMs (hereinafter described as "SAM (B 1) up to (B13)") were prepared as above and used in experiments.

TABLE 2

|        | OH  | COOH |
|--------|-----|------|
| SAM(B1) | 100 |      |
| SAM(B2) | 90  | 10   |
| SAM(B3) | 80  | 20   |
| SAM(B4) | 70  | 30   |
| SAM(B5) | 65  | 35   |
| SAM(B6) | 60  | 40   |
| SAM(B7) | 55  | 45   |
| SAM(B8) | 50  | 50   |
| SAM(B9) | 40  | 60   |
| SAM(B10) | 30 | 70   |
| SAM(B11) | 20 | 80   |
| SAM(B12) | 10 | 90   |
| SAM(B13) |    | 100  |

(Used Culture Medium)

As a serum-free culture medium, STK1 (trade name) and STK2 (trade name) (both are products of DS Pharma Biomedical Co., Ltd.) were used. Although STK1 and STK2 contain human serum albumin, transferrin, and several types of growth factor proteins, they are serum-free culture media containing no unidentified substance at all.

Further, in some experiments Dulbecco's modified Eagle's medium (DMEM) (by Sigma-Aldrich, Inc., St. Louis, Mo., USA) containing 10% fetal bovine serum (hereinafter described as "FBS") (HyClone, by Thermo Fischer Scientific Inc., Logan, Utah, USA) and 1% Antibiotic-Antimycotic (by Invitrogen, Carlsbad, Calif., USA) as a reference example (hereinafter described as "serum culture medium A", or "DMEM+10% FBS").

Further, in some experiments a 24-well microplate (24 Well Cell Culture Microplate, diameter 16 mm, by Corning Life Sciences), which was a tissue culture dish (polystyrene treated with plasma) (hereinafter described as "ordinary culture dish" or "control"), were used.

(Experiments 1 to 6)

Influence of a combination of functional groups on an SAM surface on adhesion and proliferation of a human bone marrow mesenchymal stem cell (h-BM MSC) was tested. Mesenchymal stem cells are called occasionally as MSC.

(Used Cell)

Human bone marrow mesenchymal stem cells (2 strains: R-44 and R-81) were isolated from an iliac bone by the method of Igarashi, et al. (Igarashi A, et al., Tissue Eng., 2007). They were cultured in the serum culture medium A at 37° C. under a condition of 5% $CO_2$, exchanging the culture medium every 3 days. For experiments, cells of 4th to 7th passage were used. Cells were proliferated to quasi-confluence, and thereafter incubated with trypsin and EDTA for 5 min thereby dispersing the cells.

Then an enzyme reaction was terminated with a culture medium containing 10% FBS, and the cells were washed 3 times with a serum-free DMEM. Thereafter, the cells were dispersed in a serum-free culture medium (STK1 or STK2), or in the serum culture medium A, and inoculated on to an SAM.

(Cell Culture on SAM)

A preserved SAM substrate (diameter approx. 15 mm) was washed 3 times with PBS (phosphate buffer physiological saline solution) and placed on a 24-well suspension culture plate (a culture dish for suspension cell culture, without plasma treatment, diameter approx. 16 mm, by Greiner Bio-One).

After harvesting human bone marrow mesenchymal stem cells having been cultured in advance, 0.5 mL of the cell suspension was inoculated per each cultivation system at a density of 2000 cells/$cm^2$.

Combinations of a human bone marrow mesenchymal stem cell (h-BM MSC), a culture medium and an SAM used in experiments were shown in Table 3.

TABLE 3

| Exp. | Cells | Media | SAM |
|------|-------|-------|-----|
| 1 | h-BM MSC(R44-P7) | STK2 | SAM(A1)~(A28) |
| 2 | h-BM MSC(R44-P5) | STK2 | SAM(A1)~(A20) |
| 3 | h-BM MSC(R81-P4) | STK2 | SAM(A1)~(A20) |
| 4 | h-BM MSC(R44-P5) | STK2 | SAM(B1)~(B13) |
| 5 | h-BM MSC(R44-P7) | DMEM + 10% FBS | SAM(A1)~(A28) |
| 6 | h-BM MSC(R44-P5) | DMEM + 10% FBS | SAM(A1)~(A20) |

(Evaluation Technique)

After a cell culture, its condition and shape were observed under a phase microscope and classified into adhesion-extension cells (adherent cells, A) and non-adherent cells or weakly adhered spherical cells (floating cells, F).

Evaluation of cell proliferation was conducted by measurements according to MTT assay using WST assay (Dye: WST-8 (2-(2-methoxy-4-nitrophenyl)-3-(4-nitrophenyl)-5-(2,4-disulfophenyl)-2H-tetrazolium), absorbance measurement: 450 nm).

The cell number was measured with Cell Counting Kit-8 (by Wako) using the WST-8, or Coulter Counter (by Beckman Coulter Inc.).

In some experiments, DNA was measured with a PicoGreen dsDNA Quantitation kit (by Molecular Probes, Inc.).

(Results)

Figure 3A:
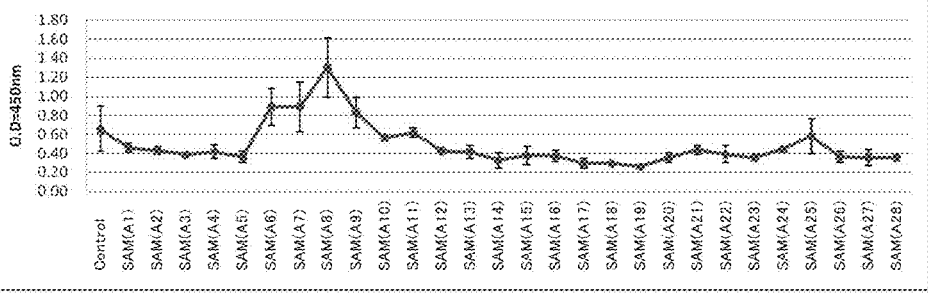
FIG. 3A is a diagram showing the MTT assay result after 4-day culture in Experiment 1.
Figure 3B:
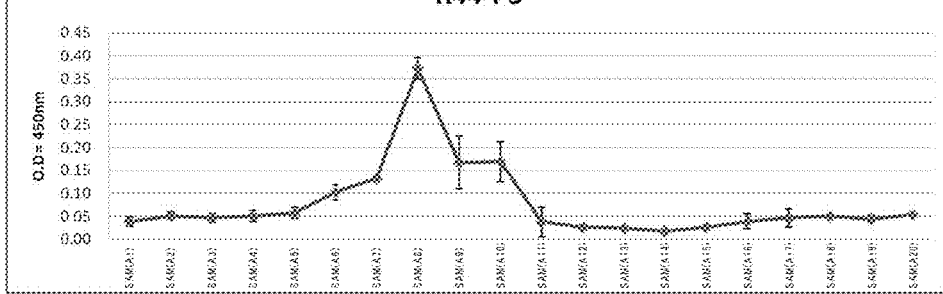
FIG. 3B is a diagram showing the MTT assay result after 4-day culture in Experiment 2.
Figure 3C:
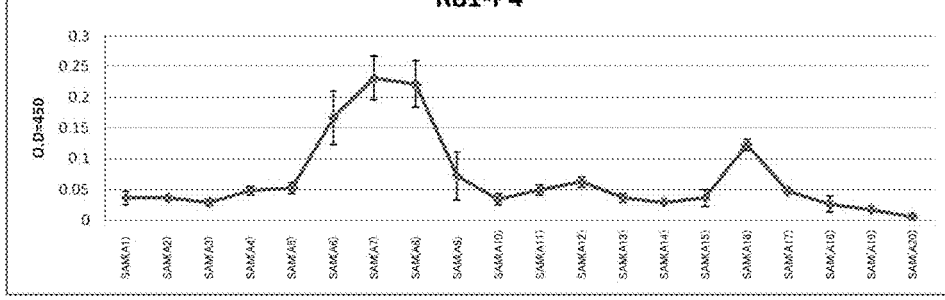
FIG. 3C is a diagram showing the MTT assay result after 4-day culture in Experiment 3.
Figure 4A:
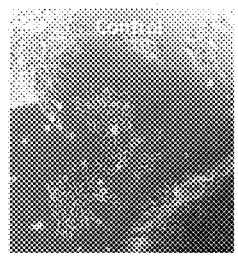
FIG. 4A is a photograph of a control.
Figure 4B:
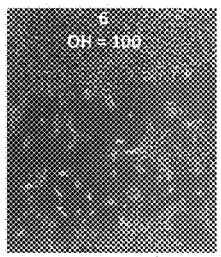
FIG. 4B is of SAM (A6)
Figure 4C:
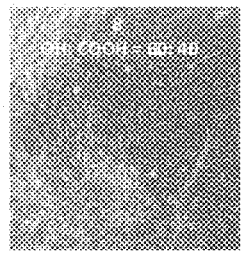
FIG. 4C is of SAM (A8)
Figure 4D:
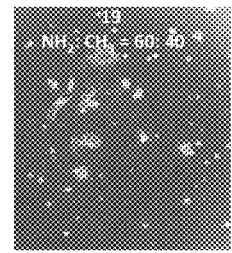
FIG. 4D is of SAM (A19)
Figure 5A:
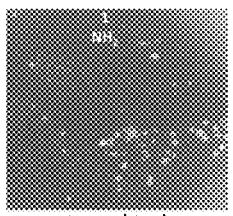
FIG. 5A is a photograph of SAM (A1)
Figure 5B:
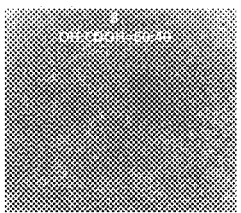
FIG. 5B is of SAM (A8)
Figure 5C:
FIG. 5C is of SAM (A14)
Figure 5D:
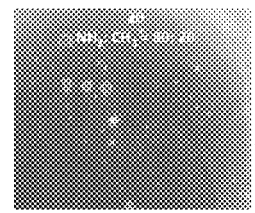
FIG. 5D is of SAM (A20)
Figure 6A:
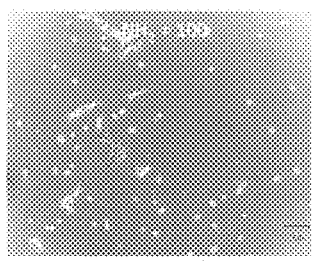
FIG. 6A is a photograph of SAM (A1)
Figure 6B:
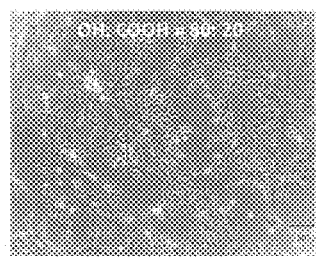
FIG. 6B is of SAM (A7)
Figure 6C:
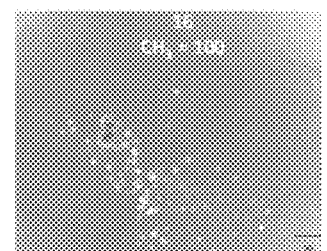
FIG. 6C is of SAM (A16)

The MTT assay results after 4-day culture in Experiments 1, 2, and 3 are shown in FIGS. 3A, B, and C, and photographs after 4-day culture in Experiments 1, 2, and 3 are shown in FIG. 4, FIG. 5, and FIG. 6, respectively.

Human bone marrow mesenchymal stem cells (R44, and R81 strains) adhered, irrespective of a type of donor or a subculture number (4 to 7 times), to SAMs (A5) to (A11) at a high level, and adhered also to SAMs (A12) to (A13) at a low level. They did however substantially not adhere to SAMs (A1) to (A4), and (A14) to (A28) having different compositions.

The cells proliferated well with SAMs (A6) to (A8) (relative content from OH=100 to OH:COOH=60:40) irrespective of a donor or a passage number, proliferated also with SAM (A9) and SAM (A16), but did not proliferate with other SAM compositions. The cell proliferation was maximum with SAM (A7) (OH:COOH=80:20) or SAM (A8) (OH:COOH=60:40).

Next, with respect to SAMs (B1) to (B13) prepared with smaller intervals in the functional group content of the SAM composition (OH:COOH), to which human bone marrow mesenchymal stem cells adhered, Experiment 4 was carried out. The results of cell number measurement are shown in FIG. 7, photographs of the cultured cells are shown in FIG. 8. In the experiment, a cell number was measured directly with a Coulter counter.

It is clear that with SAM (B5) to SAM (B11) (OH:COOH=65:35 to 30:70) cells proliferated better than with the control, and proliferation of human bone marrow mesenchymal stem cells was maximum with SAM (B5) (OH:COOH=65:35).

(Influence of SAM in Presence of Serum)

FIG. 9A and FIG. 9B show MTT assay results of Experiments 5 and 6 after 4-day culture carried out using the serum culture medium A, and FIG. 10 is photographs after 4-day culture in Experiment 5, showing that human bone marrow mesenchymal stem cells (R44 strain) adhered to all the SAM compositions (A1) to (A28). Probably, this is because cells were not vulnerable to an influence of an SAM composition owing to the presence of an adhesion factor in serum, and adhered to all the SAMs. In this connection, the degree of proliferation differs depending on the SAM composition, and the proliferation is remarkable with SAMs (A1) to (A5), SAMs (A10) to (A12), and SAMs (A17) to (A24).

Noteworthily, SAMs (A6) to (A9), which promoted proliferation in a serum-free culture medium, suppressed proliferation in the serum culture medium A. It can be understood that some serum protein adhered to SAMs (A6) to (A8) and obstructed proliferation.

Further, many of SAM compositions, which suppressed adhesion and proliferation in a serum-free culture medium, promoted proliferation in the serum culture medium A. It is believed that an adhesion factor or a proliferation promotion factor in serum bonded to the SAM compositions. In other words, it has become clear that the influence of an SAM composition on adhesion and proliferation of cells is substantially different in the presence of serum and in the absence of serum.

Figure 11:
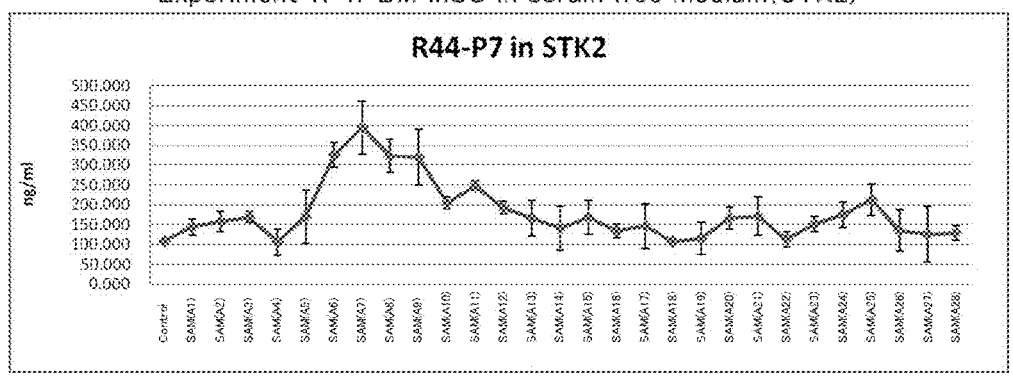
FIG. 11 is a diagram showing the results of DNA determinations after 4-day culture in Experiment 1.
Figure 12:
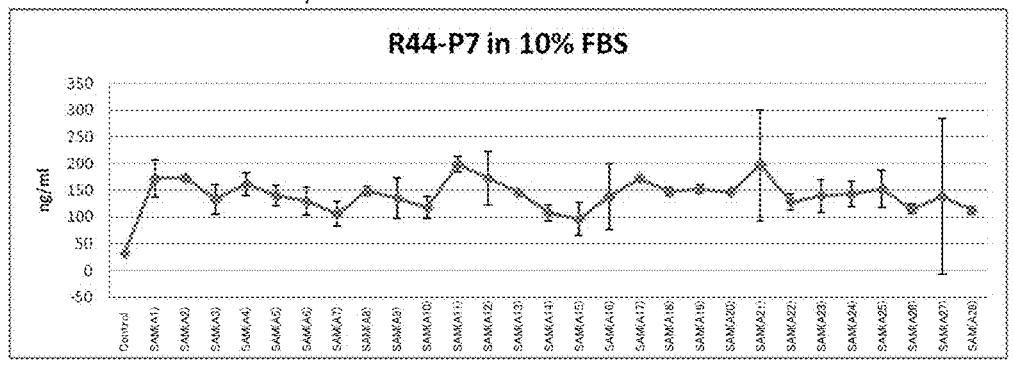
FIG. 12 is a diagram showing the results of DNA determinations after 4-day culture in Experiment 5.

In some experiments (Experiments 1 and 5), proliferation was evaluated also by means of DNA determination. FIG. 11 and FIG. 12 show respectively the DNA determination results of Experiment 1 and Experiment 5 after 4-day culture. The MTT assay results and the DNA determination results coincided.

Figure 13A:
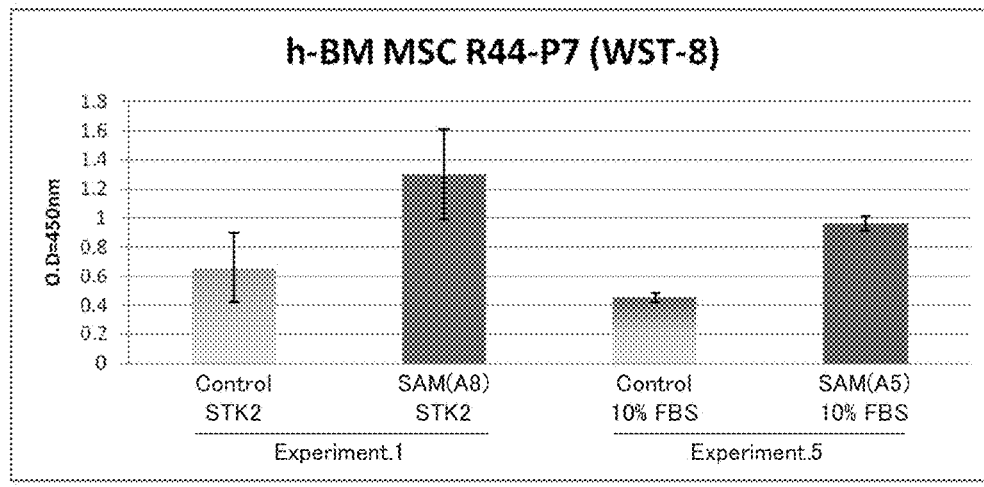
FIG. 13A is a diagram showing the results of MTT assays after 4-day culture with an ordinary culture dish and SAM (A8) in Experiment 1 and with an ordinary culture dish and SAM (A5) in Experiment 5.
Figure 13B:
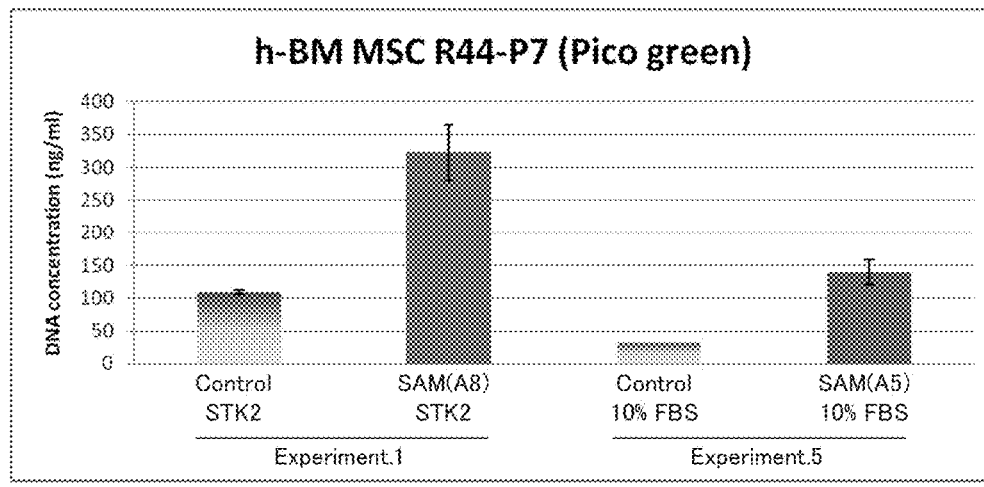
FIG. 13B is a diagram showing the results of DNA determinations after 4-day culture with an ordinary culture dish and SAM (A8) in Experiment 1 and with an ordinary culture dish and SAM (A5) in Experiment 5.

FIG. 13A shows the MTT assay results and FIG. 13B shows the DNA determination results respectively of Experiment 1 with an ordinary culture dish and SAM (A8), and Experiment 5 with an ordinary culture dish and SAM (A5) after 4-day culture, and it becomes clear therefrom that the cell number and the DNA increase 2 to 3-fold after 4-day culture with SAM (A8) in a serum-free culture medium compared to with an ordinary culture dish.

From the above experimental results it becomes clear that a combination of an SAM, whose surface content ratio of hydroxyl group:carboxyl group is from 100:0 to 0:100, preferably, from 80:20 to 20:80, and more preferably from 70:30 to 60:40, and a serum-free culture medium (STK2) can promote adhesion and proliferation of human bone marrow mesenchymal stem cells even in a serum-free culture medium.

(Experiments 11 to 13)

Influence of functional group content on an SAM surface on adhesion and proliferation of rat primary mesenchymal stem cells (rat-primary MSC) was tested.

A bone marrow fluid contains hematopoietic cells, vascular cells, interstitial cells, mesenchymal stem cells and the like. Namely it is a heterogeneous cell population. Bone marrow mesenchymal stem cells are isolated as fibroblast-like cells in bone marrow, which adhere to a culture dish and extend. However, it is difficult to obtain homogeneous bone marrow mesenchymal stem cells with an ordinary culture dish. Consequently, in the present experiment, a rat bone marrow fluid was inoculated directly in various types of SAM culture dishes and influence of the SAM composition on adhesion and proliferation of mesenchymal stem cells (fibroblast-like cells) was investigated.

A bone marrow fluid separated from right and left femora and tibiae of five 5-week old male Wistar rats was diluted with a serum-free αMEM to 25 mL ("diluted bone marrow fluid").

In a culture dish provided with various SAM substrates the diluted bone marrow fluid was inoculated in an amount of 0.06 mL/16 mm-well, and further STK1, the serum culture medium A, or αMEM containing 10% fetal bovine serum (FBS) (hereinafter described as "αMEM+10% FBS") was added so that the total amount of the culture media became 0.5 mL/well.

The culture was continued for 7 to 8 days, while exchanging the culture medium after 3 days every 3 days.

In order to obtain rat bone marrow mesenchymal stem cells of the 2nd passage or further, 3 mL of the diluted bone marrow fluid was inoculated in a 100 mm-tissue culture dish (by Corning Incorporated) and cultured for 8 days, and thereafter cells dispersed with trypsin and EDTA out of the subconfluent cultivation system were inoculated to each type of SAM substrate at a cell density of 2000/cm$^2$.

The evaluation methods for cell shape observation and cell number are similar to Experiments 1 to 6. Combinations of cells, culture media, and SAMs used are shown in Table 4.

TABLE 4

| Exp. | Cells | Media | SAM |
|---|---|---|---|
| 11 | rat-primary MSC | STK1 | SAM(A1)~(A28) |
| 12 | rat-primary MSC | DMEM + 10% FBS | SAM(A1)~(A28) |
| 13 | rat-primary MSC | αMEM + 10% FBS | SAM(A1)~(A28) |

(Results)

Figure 14A:
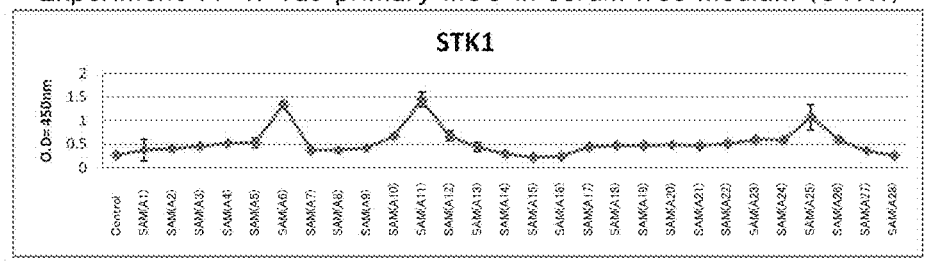
FIG. 14A is a diagram showing the results of MTT assays after 7-day culture in Experiment 11-1.
Figure 14B:
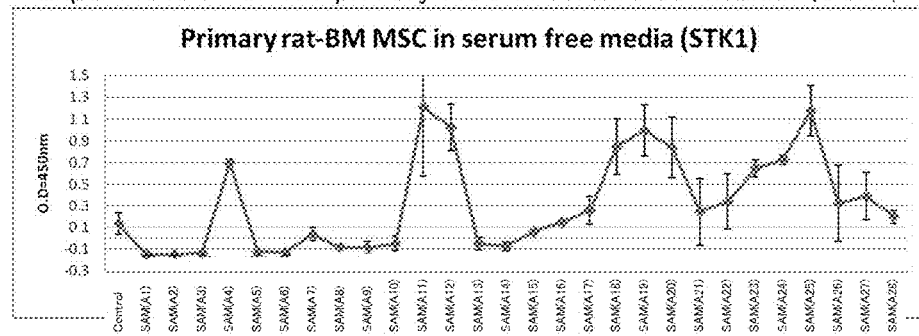
FIG. 14B is a diagram showing the results of MTT assays after 8-day culture in Experiment 11-2.
Figure 14C:
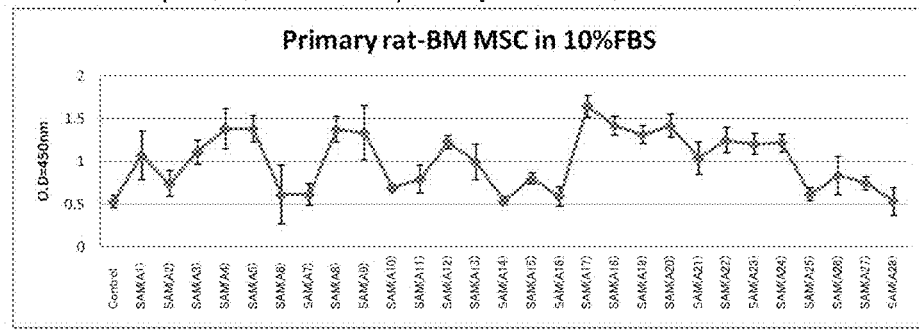
FIG. 14C is a diagram showing the results of MTT assays after 8-day culture in Experiment 12.
Figure 14D:
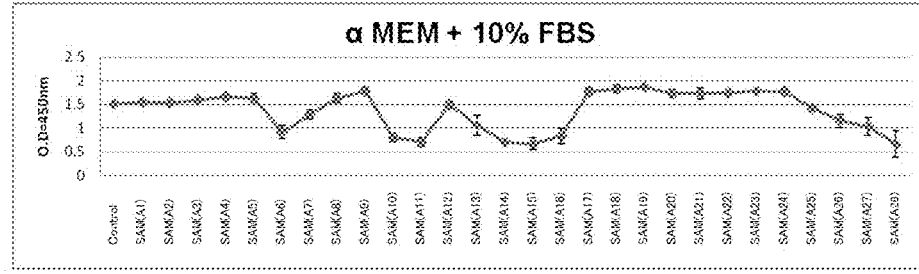
FIG. 14D is a diagram showing the results of MTT assays after 7-day culture in Experiment 13.
Figure 15A:
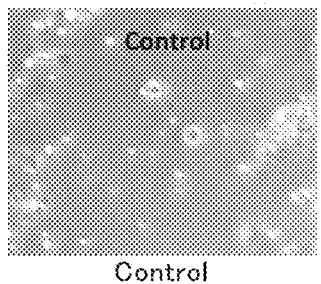
FIG. 15A is a photograph of a control.
Figure 15B:
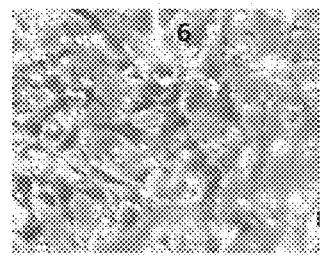
FIG. 15B is of SAM (A6)
Figure 15C:
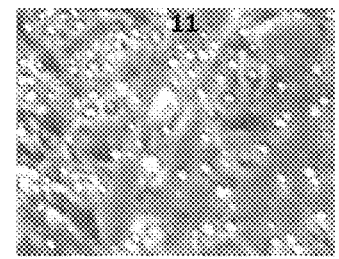
FIG. 15C is of SAM (A11)
Figure 15D:
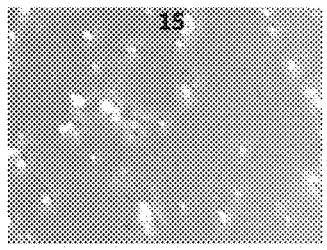
FIG. 15D is of SAM (A15)
Figure 15E:
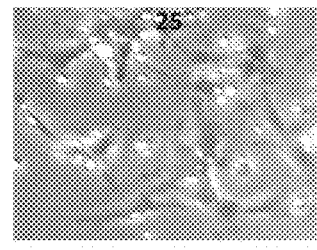
FIG. 15E is of SAM (A25)
Figure 16A:
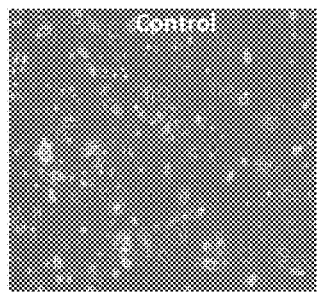
FIG. 16A is a photograph of a control.
Figure 16B:
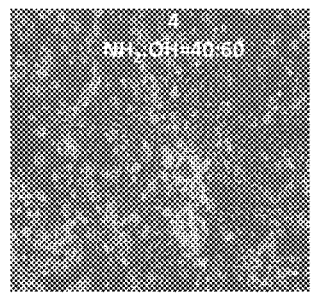
FIG. 16B is of SAM (A4)
Figure 16C:
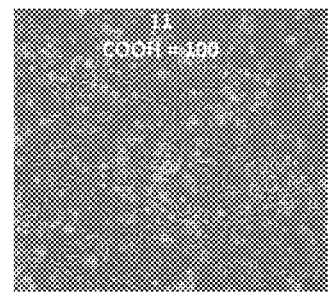
FIG. 16C is of SAM (A11)
Figure 16D:
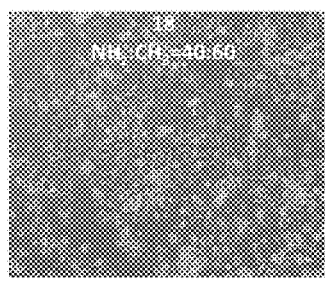
FIG. 16D is of SAM (A18)
Figure 16E:
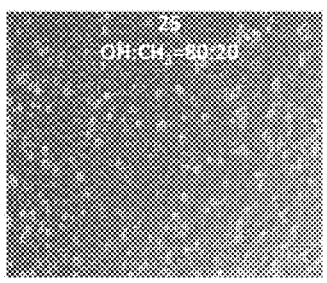
FIG. 16E is of SAM (A25)
Figures 17A, 17B, 17C, 17D:
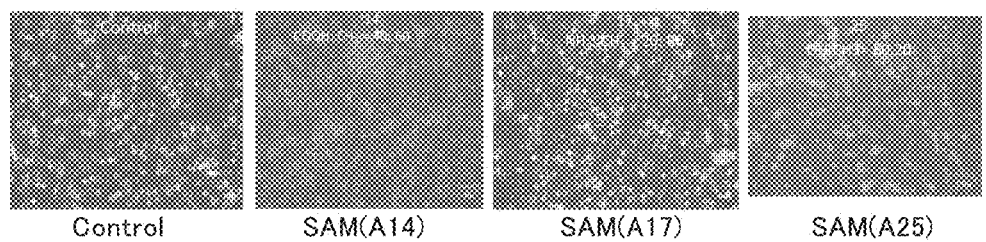
FIG. 17A is a photograph of a control.
FIG. 17B is of SAM (A14)
FIG. 17C is of SAM (A17)
FIG. 17D is of SAM (A25)
Figures 18A, 18B, 18C:
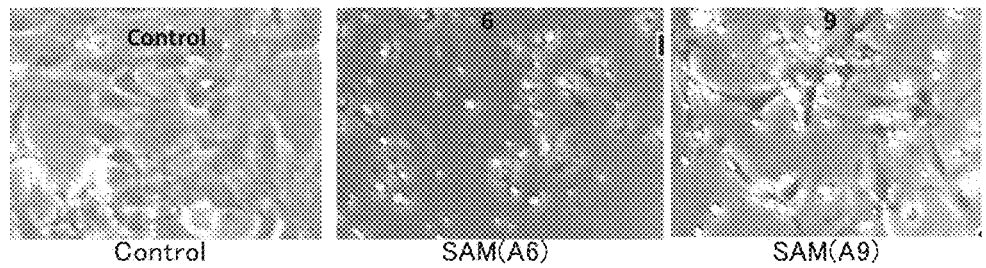
FIG. 18A is a photograph of a control.
FIG. 18B is of SAM (A6)
FIG. 18C is of SAM (A9)
Figures 18D, 18E, 18F:
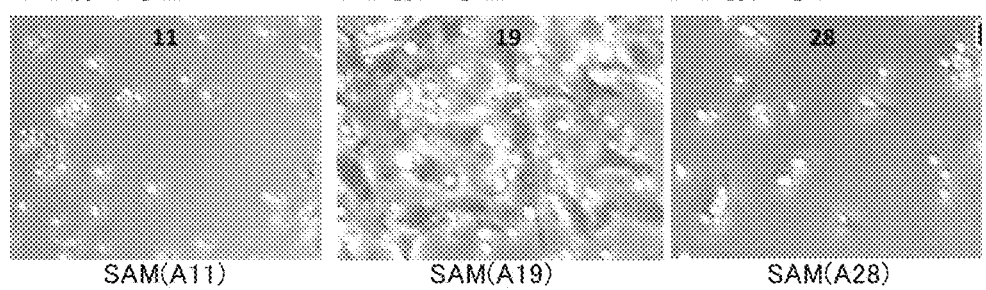
FIG. 18D is of SAM (A11)
FIG. 18E is of SAM (A19)
FIG. 18F is of SAM (A28)

In Experiment 11 cultures were carried out for 7 days and 8 days and evaluated respectively. Hereinafter a 7-day culture in Experiment 11 is described as "Experiment 11-1" and an 8-day culture in Experiment 11 is described as "Experiment 11-2". MTT assay results of Experiment 11-1 after 7-day cultures are shown in FIG. 14A, MTT assay results of Experiment 11-2 after 8-day cultures are in FIG. 14B, MTT assay results of Experiment 12 after 8-day cultures are in FIG. 14C, and MTT assay results of Experiment 13 after 7-day cultures are in FIG. 14D. Photographs of Experiment 11-1 after 7-day cultures are shown in FIG. 15, photographs of Experiment 11-2 after 8-day cultures are in FIG. 16, photographs of Experiment 12 after 8-day cultures are in FIG. 17, and photographs of Experiment 13 after 7-day cultures are in FIG. 18.

Fibroblast-like cells (including mesenchymal stem cells) of rat bone marrow proliferated in the presence of the serum-free culture medium STK1 with SAMs (A4), (A6), (A11), (A12), (A17) to (A20), (A23) to (A25) as other group. Moreover, after 7 to 8 day-culture the cell number 7 to 11 times as large as that with an ordinary culture dish was obtained. Taking advantage of difference in SAM adherence, classification of fibroblast-like cells (mesenchymal stem cells) in bone marrow is possible.

Meanwhile, also in the presence of the serum culture medium A or αMEM+10% FBS, with respect to some SAMs enhancement of proliferation beyond an ordinary culture dish was observed. It means that proliferation patterns of rat bone marrow fibroblast-like cells (mesenchymal stem cells) in the presence of serum and in the absence of serum are different.

From the above experimental results it becomes clear that adhesion and proliferation of primary rat bone marrow mesenchymal stem cells can be promoted by a combination of an SAM, on which surface amino group:hydroxyl group is 40:60, carboxyl group:methyl group from 100:0 to 80:20, amino group:methyl group from 20:80 to 80:20, amino group:carboxyl group from 40:60 to 20:80, or hydroxyl group:methyl group from 100:0 to 80:20, and the serum-free culture medium (STK1), even in a serum-free culture medium.

(Experiments 21 to 23)

Influence of functional group content on an SAM surface on adhesion and proliferation of mesenchymal stem cells derived from various tissues was tested.

Two strains of human synovial membrane-derived mesenchymal stem cells (also called as human osteoarthritis-derived mesenchymal stem cells, or synovial fibroblast, (h-synovial MSC(S6-P2) and h-synovial MSC)) were obtained from Cell Applications Inc.

A strain of human dental pulp mesenchymal stem cells (h-Dental pulp MSC) was isolated as a cell population migrated and proliferated from a pulp tissue strip of an extracted third molar (Odontoblast Differentiation of Human Dental Pulp Cells in Explant Cultures, M. L. Couble, et al., Calcif. Tissue Int., 2000).

The cells were cultured in the serum culture medium A at 37° C. under a condition of 5% $CO_2$, exchanging the culture medium every 3 days. For subculturing a subconfluent culture system was incubated with trypsin and EDTA for 5 min Then an enzyme reaction was terminated with a 10% FBS-containing culture medium, followed by centrifugation and the cells were washed 3 times with a serum-free DMEM. Then the cells suspended in the STK2 or STK1 were inoculated in an SAM culture dish at a cell density of 2000/cm$^2$ in Experiments 21, 23 and 500/cm$^2$ in Experiment 22, and cultured for 4 to 14 days.

The evaluation methods for cell shape observation and cell number are similar to Experiments 1 to 6. Combinations of cells, culture media, and SAMs used are shown in Table 5.

TABLE 5

| Exp. | Cells | Media | SAM |
| --- | --- | --- | --- |
| 21 | h-synovial MSC (S6-P2) | STK2 | SAM(A1)~(A20) |
| 22 | h-synovial MSC | STK1 | SAM(A1)~(A28) |
| 23 | h-dental pulp MSC (P5) | STK2 | SAM(A1)~(A20) |

(Results)

Figure 19A:
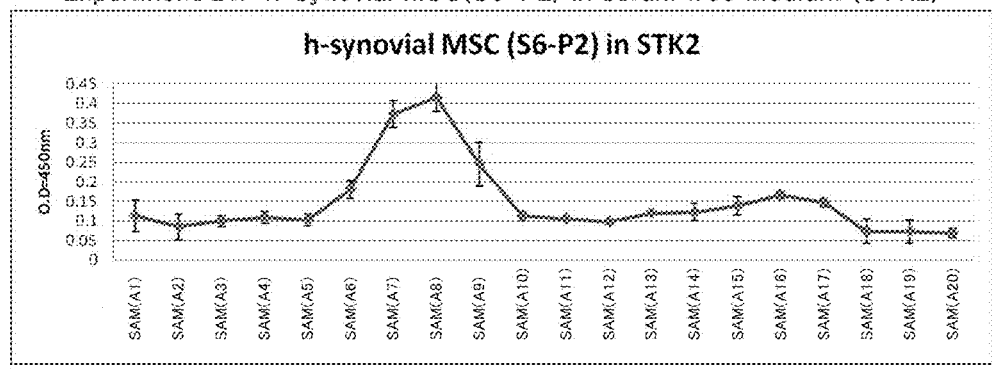
FIG. 19A is a diagram showing the results of MTT assays after 4-day culture in Experiment 21.
Figure 19B:
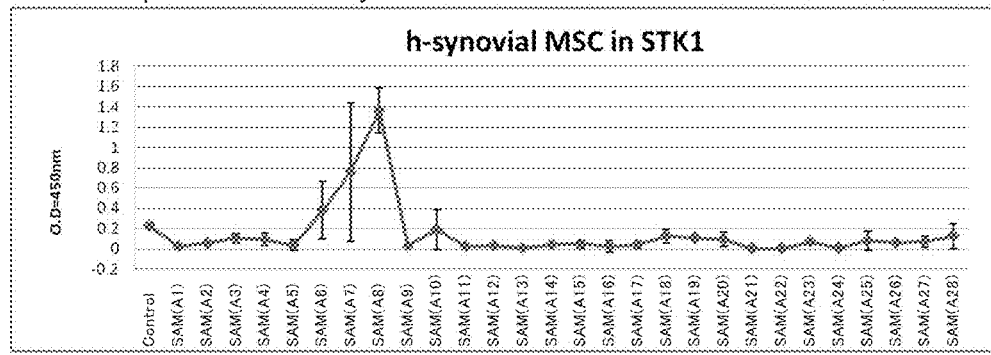
FIG. 19B is a diagram showing the results of MTT assays after 14-day culture in Experiment 22.

MTT assay results in Experiment 21 are shown in FIG. 19A, MTT assay results in Experiment 22 are shown in FIG. 19B, respectively; photographs after 4-day culture in Experiment 21 are shown in FIG. 20, and photographs after 14-day culture in Experiment 22 are shown in FIG. 21, respectively.

Human synovial membrane-derived mesenchymal stem cells (2nd passage) adhere well to SAMs (A6) to (A9) irrespective of difference in a donor or the type of serum-free culture media (STK2 or STK1), and adhere also to SAMs (A10) and (A11), but not to SAMs with other compositions.

The cells proliferated well with SAMs (A6) to (A8), (relative contents from OH=100 to OH:COOH=60:40), proliferated also with SAM (A9) but not with other compositions.

The maximum cell proliferation was observed with SAM (A7) (OH:COOH=80:20) or SAM (A8) (OH:COOH=60:40). As shown in FIG. 19B, a cell number 7 times as large as that with an ordinary culture dish was obtained. The result coincided substantially with the SAM composition that promoted proliferation of human bone marrow mesenchymal stem cells.

Therefore it becomes clear that a combination of an SAM, whose surface content ratio of hydroxyl group:carboxyl group is from 100:0 to 40:60, and preferably from 80:20 to 60:40, and a serum-free culture medium (STK2 or STK1) can promote adhesion and proliferation of human synovial membrane-derived mesenchymal stem cells even in a serum-free culture medium.

MTT assay results after 4-day culture in Experiment 23 are shown in FIG. 22, and photographs thereof are shown in FIG. 23. An SAM composition that promotes proliferation of human dental pulp-derived mesenchymal stem cells (5th passage) was substantially common to human bone marrow mesenchymal stem cells and human synovial membrane-derived mesenchymal stem cells. Consequently, it becomes clear that a combination of an SAM, whose surface content ratio of hydroxyl group:carboxyl group is from 100:0 to 60:40, and the serum-free culture medium (STK2) can promote adhesion and proliferation of human dental pulp-derived mesenchymal stem cells even in a serum-free culture medium.

(Experiments 31 to 33)

Influence of functional group content on a culture dish surface on adhesion and proliferation of human fibroblasts and rat osteoblasts was tested.

Human dermal fibroblasts were purchased from Kurabo Industries Ltd. (Osaka) and preserved as above in the serum culture medium A.

Rat cranial bone-derived osteoblasts were isolated by a method by Yoshiko, et al. (A subset of osteoblasts expressing high endogenous levels of PPAR gamma switches fate to adipocytes in the rat calvaria cell culture model. Yoshiko Y, Oizumi K, Hasegawa T, Minamizaki T, Tanne K, Maeda N, Aubin J E, PLoS One, 2010, 5 (7): e11782).

Namely, a calvarium of a male Wistar rat on embryonic day 21 was digested with time by collagenase and fractionated to 5 fractions, of which 4 fractions except the first fraction (fibroblast fraction) were cultured independently with 10% FBS-containing αMEM. The fractions were combined next day and cultured with the same culture medium added with ascorbic acid (50 µg/mL). The cells were proliferated to quasi-confluence, and then subcultured with trypsin and EDTA as above.

The evaluation methods for cell shape observation and cell number are similar to Experiments 1 to 6. Combinations of cells, culture media, and SAMs used are shown in Table 6. Meanwhile, the cells were inoculated in a culture dish at a cell density of 2000/cm$^2$.

TABLE 6

| Exp. | Cells | Media | SAM |
| --- | --- | --- | --- |
| 31 | h-fibroblast (1429-P8) | STK2 | SAM(A1)~(A28) |
| 32 | h-fibroblast (1429-P8) | DMEM + 10% FBS | SAM(A1)~(A28) |
| 33 | rat-osteoblasts (P1) | STK2 | SAM(A1)~(A28) |

(Results)

MTT assay results in Experiment 31 are shown in FIG. 24A, MTT assay results in Experiment 32 are shown in FIG. 24B, respectively; and photographs after 4-day culture in Experiment 31 are shown in FIG. 25.

As seen in FIG. 24A, human fibroblasts adhered well to SAMs (A6) to (A9) and SAMs (A25) to (A28) in the presence of a serum-free culture medium (STK2). They proliferated best with SAMs (A6) and (A7) (from OH=100 to OH:COOH=80:20) and SAMs (A25) and (A26) (from OH:CH$_3$=80:20 to OH:CH$_3$=60:40).

With the SAM compositions, the cell number 2-fold or more the number with an ordinary culture dish was obtained within 4 days. The fibroblasts proliferated moderately also with SAMs (A8), (A27) and (A28), but did not proliferate with other compositions. The SAM compositions that proliferated human fibroblasts in a serum-free culture medium overlapped partly the SAM compositions that proliferated human mesenchymal stem cells, but their patterns were different.

From the above, it becomes clear that adhesion and proliferation of human fibroblasts can be promoted by a combination of an SAM, on which surface hydroxyl group: carboxyl group is at a content ratio from 100:0 to 40:60, or hydroxyl group:methyl group is at a content ratio from 80:20 to 20:80, preferably hydroxyl group:carboxyl group at a content ratio from 100:0 to 80:20, or hydroxyl group:methyl group at a content ratio from 80:20 to 60:40, and the serum-free culture medium (STK2), even in a serum-free culture medium.

When human fibroblasts were cultured in the serum culture medium A, they adhered and proliferated with the compositions other than SAMs (A6), (A14) to (A16), (A25), and (A26). Especially with SAMs (A1) to (A5), (A8), (A17), and (A20) to (A24) they adhered well and proliferated better than in an ordinary culture dish. Further, when the serum culture medium A was used, the pattern of proliferation of human fibroblasts with various SAMs was similar to human bone marrow mesenchymal stem cells and rat bone marrow mesenchymal stem cells. Namely, in the presence of serum, the cell type or animal species could not be discriminated.

MTT assay results after 4-day culture in Experiment 33 using rat osteoblasts are shown in FIG. 26, and photographs are shown in FIG. 27. The rat osteoblasts adhered well to SAMs (A6) to (A12) and (A25) to (A28) in the presence of a serum-free culture medium (STK2). And with respect to all the SAM compositions cell proliferation higher than in an ordinary culture dish was observed. They proliferated best with SAMs (A6) to (A7), (A10) to (A11) and (A25) to (A28) (from $OH:CH_3=80:20$ to $OH:CH_3=20:80$). The SAM compositions, with which osteoblasts proliferated in a serum-free culture medium, were different from patterns for mesenchymal stem cells or fibroblasts.

From the above results, it becomes clear that adhesion and proliferation of rat osteoblasts can be promoted by a combination of an SAM, on which surface hydroxyl group: carboxyl group is at a content ratio from 100:0 to 0:100, carboxyl group:methyl group is at a content ratio 80:20, or hydroxyl group:methyl group at a content ratio from 80:20 to 20:80, and a serum-free culture medium (STK2), even in a serum-free culture medium.

(Experiments 41 to 42)

Influence of functional group content on a culture dish surface on adhesion and proliferation of rat bone marrow mesenchymal stem cells (rat-BM MSC) was tested.

Rat bone marrow mesenchymal stem cells were isolated by a technique similar to Experiments 11 to 13, cultured and used.

The evaluation methods for cell shape observation and cell number are similar to Experiments 1 to 6. Combinations of cells, culture media, and SAMs used are shown in Table 7.

TABLE 7

| Exp. | Cells | Media | SAM |
|---|---|---|---|
| 41 | rat-BM MSC | STK2 | SAM(A1)~(A28) |
| 42 | rat-BM MSC | DMEM + 10% FBS | SAM(A1)~(A28) |

(Results)

Figure 28A:
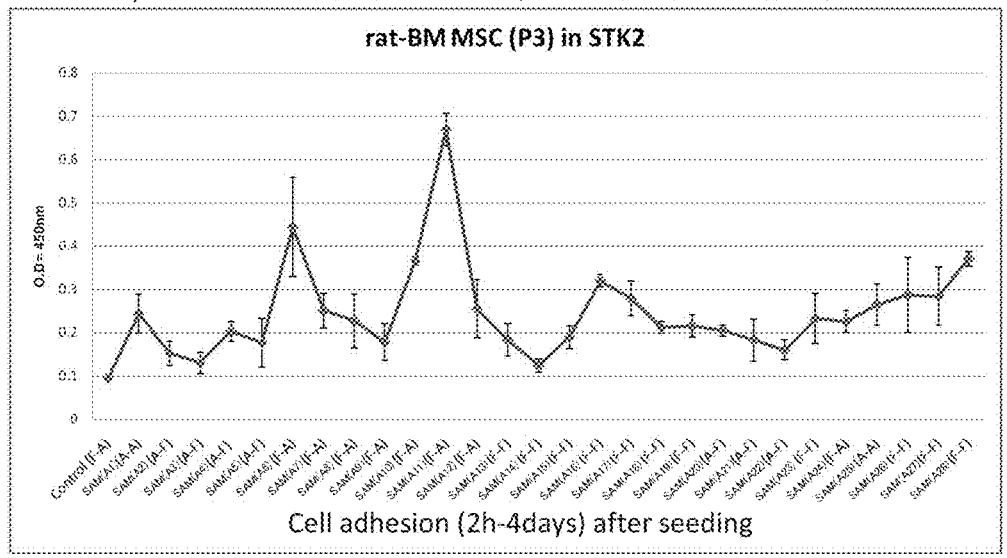
FIG. 28A is a diagram showing the results of MTT assays after 4-day culture in Experiment 41.
Figure 29A:
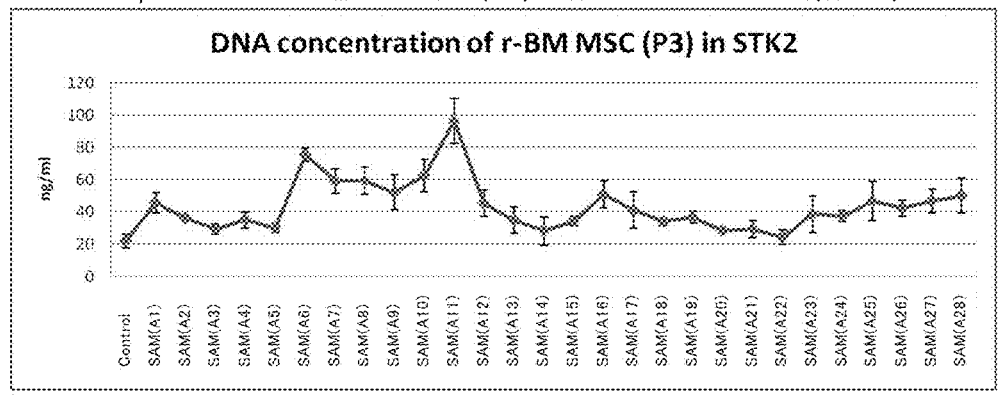
FIG. 29A is a diagram showing the results of DNA determinations after 4-day culture in Experiment 41.
Figure 29B:
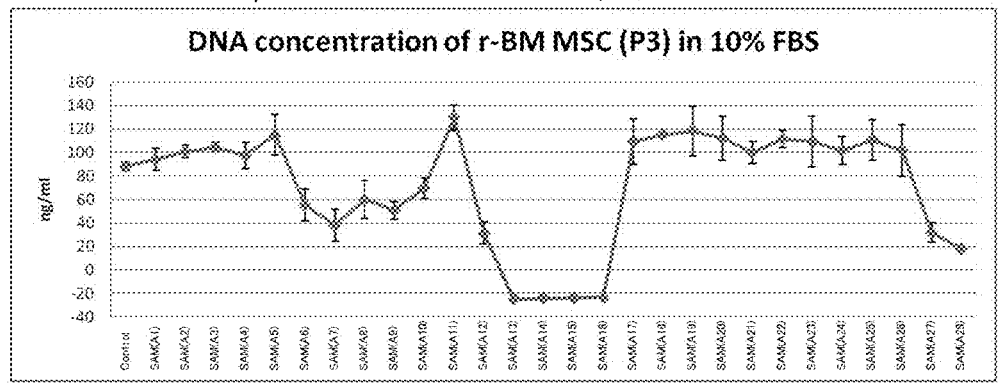
FIG. 29B is a diagram showing the results of DNA determinations after 4-day culture in Experiment 42.
Figure 31A:
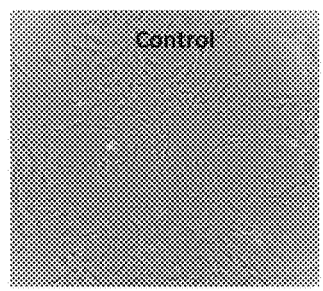
FIG. 31A is a photograph of a control.
Figure 31B:
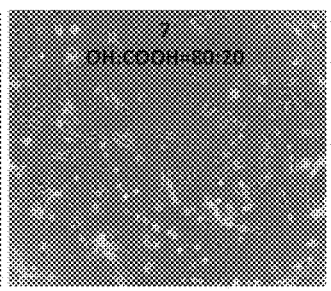
FIG. 31B is of SAM (A7)
Figure 31C:
FIG. 31C is of SAM (A11)
Figure 31D:
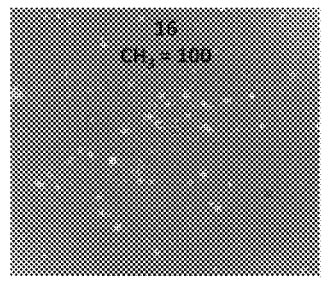
FIG. 31D is of SAM (A16)
Figure 31E:
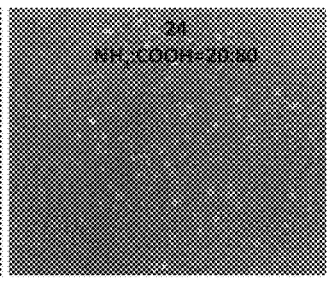
FIG. 31E is of SAM (A24)
Figure 31F:
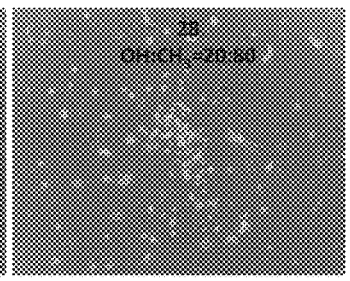
FIG. 31F is of SAM (A28)

MTT assay results after 4-day culture in Experiment 41 and Experiment 42 are shown in FIGS. 28A and B, DNA determination results after 4-day culture in Experiment 41 and Experiment 42 are shown in FIGS. 29A and B, and photographs after 4-day culture in Experiment 41 and Experiment 42 are shown in FIG. 30 and FIG. 31, respectively.

Figure 28B:
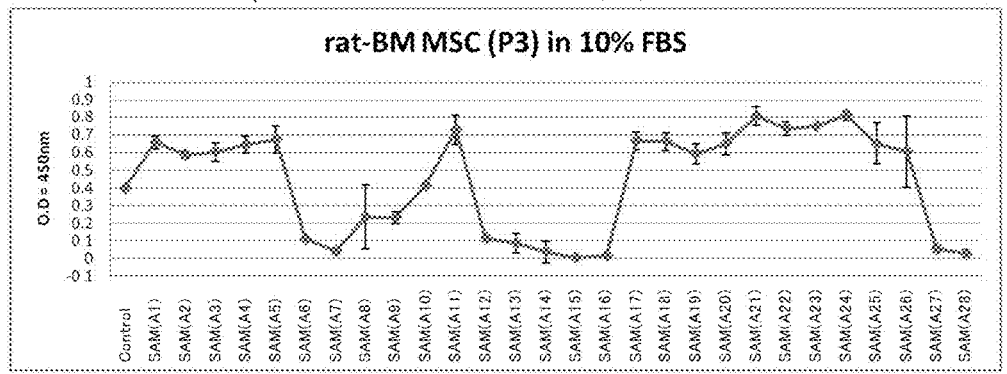
FIG. 28B is a diagram showing the results of MTT assays after 4-day culture in Experiment 42.

Practically identical tendency can be recognized between MTT assay results and DNA determination results, and remarkable proliferation of rat bone marrow mesenchymal stem cells with SAMs (A6) to (A11) in the presence of a serum-free culture medium (STK2) was observed. It is clear that adhesion and proliferation of rat bone marrow mesenchymal stem cells can be promoted by combining an SAM, on which surface hydroxyl group:carboxyl group is at a content ratio from 100:0 to 0:100, and carboxyl group: methyl group is at a content ratio from 100:0 to 80:20, and a serum-free culture medium (STK2), even in a serum-free culture medium. In this regard, the notation of 2 h-4 days in FIG. 28 refers to conditions of cell adhesion 2 hours after and 4 days after seeding, and A stands for dominantly adhered cells and F for dominantly not-adhered cells. In other words, depending on the type of SAMs, some SAMs promoted initial adhesion but did not sustain adhesion or proliferation for a long term, or some other SAMs promoted not only initial adhesion, but also proliferation. It was shown that SAM influenced not only on adhesion but also on proliferation.

(Experiments 51 and 52)

Influence of functional group content on a culture dish surface on adhesion and proliferation of human primary mesenchymal stem cells (h-primary MSC) was tested.

Human primary bone marrow mesenchymal stem cells were obtained from a bone marrow fluid of an iliac bone under the approval of the ethics committee of Hiroshima University (Kubo H, Shimizu M, Taya Y, et al., Gene to Cells, 2009, 14: 407-424).

A monocyte fraction of human bone marrow (R82 strain) was diluted in the STK1 culture medium, and 0.5 mL of the cell suspension was inoculated in each of 16-mm culture dishes at density of nucleated cells of 70,000 count/cm$^2$, followed by addition of 0.25 mL of STK1 after 3 days from the inoculation. The culture medium was exchanged with 0.5 mL of STK1 every 3 days. Then, on day 14 of the inoculation a photograph of cells was taken, and an MTT assay was conducted after addition of a WST-8 reagent to the culture medium. Inoculation was conducted identically as above except that a human bone marrow fluid (R83 strain) was used as it was, and MTT assay was carried out.

The evaluation methods for cell shape observation and cell number are similar to Experiments 1 to 6. Combinations of cells, culture media, and SAMs used are shown in Table 8.

TABLE 8

| Exp. | Cells | Media | SAM |
|---|---|---|---|
| 51 | h-primary MSC (R82) | STK1 | SAM(A1)~(A28) |
| 52 | h-primary MSC (R83) | STK1 | SAM(A6),(A7),(A8),(A9) |

(Results)

Figure 32:
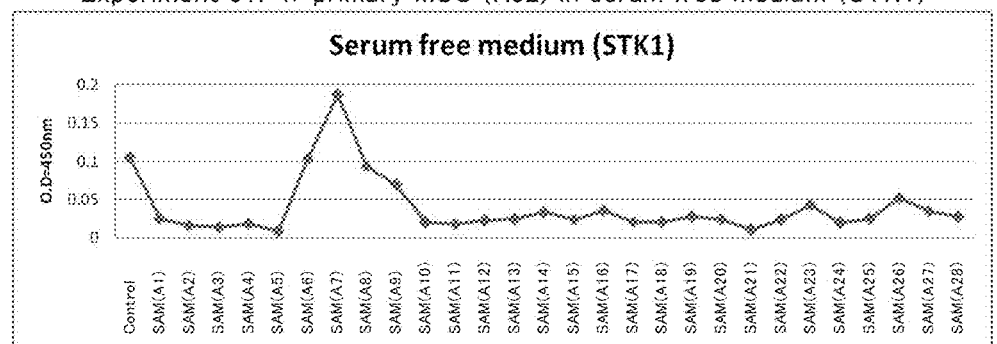
FIG. 32 is a diagram showing the results of MTT assays after 14-day culture in Experiment 51.
Figures 33A, 33B, 33C:
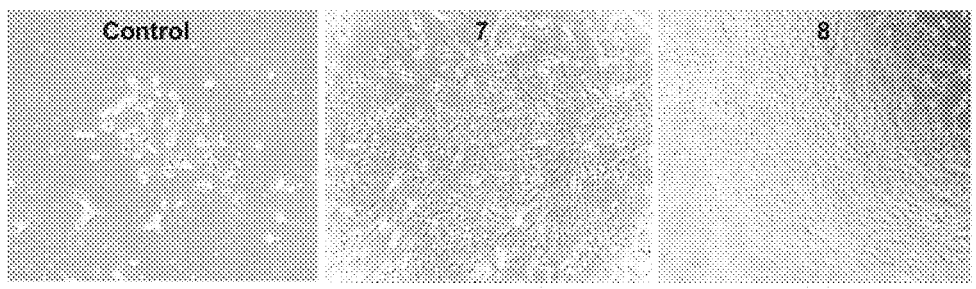
FIG. 33A is a photograph of a control.
FIG. 33B is of SAM (A7)
FIG. 33C is of SAM (A8)

MTT assay results in Experiment 51 are shown in FIG. 32, and photographs after culture are shown in FIG. 33, respectively. Remarkable proliferation of human primary mesenchymal stem cells is recognized with SAMs (A6) to (A11) in the presence of a serum-free culture medium (STK1). It is clear that adhesion and proliferation of human primary mesenchymal stem cells can be promoted by combining an SAM, on which surface hydroxyl group:carboxyl group is at a content ratio from 100:0 to 40:60, and a serum-free culture medium (STK2), even in a serum-free culture medium.

Figure 34:
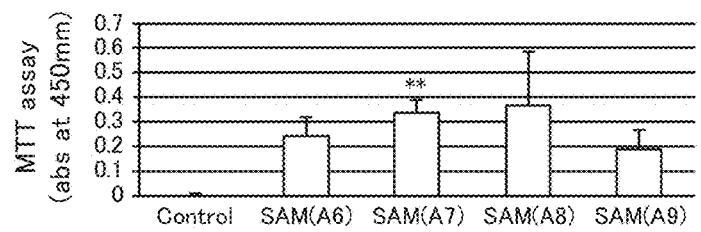
FIG. 34 is a diagram showing the results of MTT assays after 14-day culture in Experiment 52.
Figure 35A:
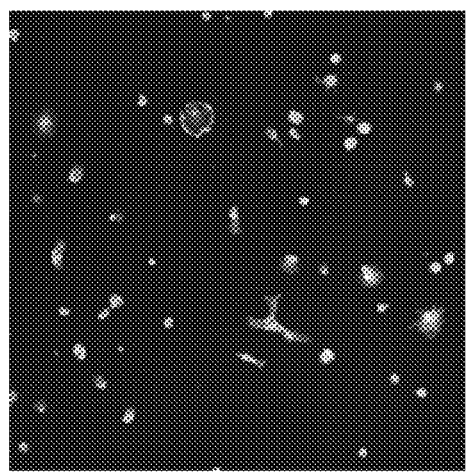
FIG. 35A is a photograph enlarged 10-fold.
Figure 35B:
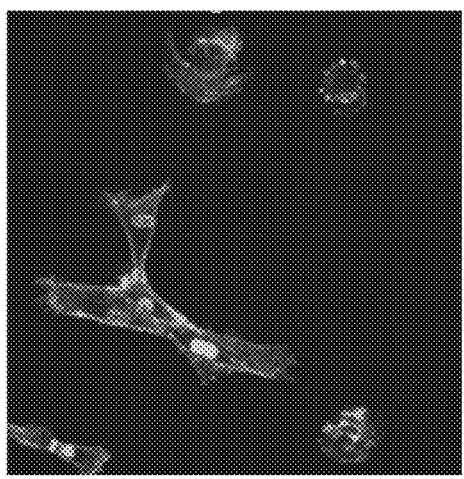
FIG. 35B is a photograph enlarged 40-fold.
Figure 36A:
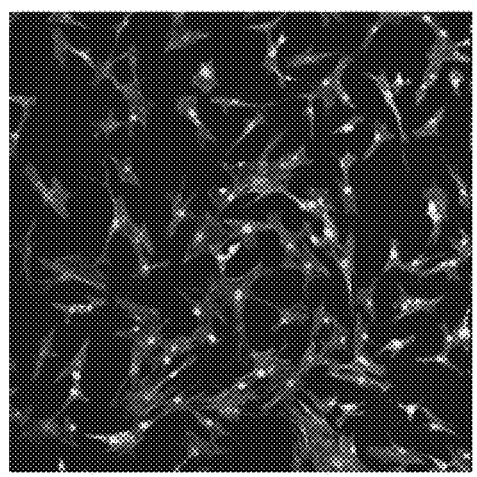
FIG. 36A is a photograph enlarged 10-fold.
Figure 36B:
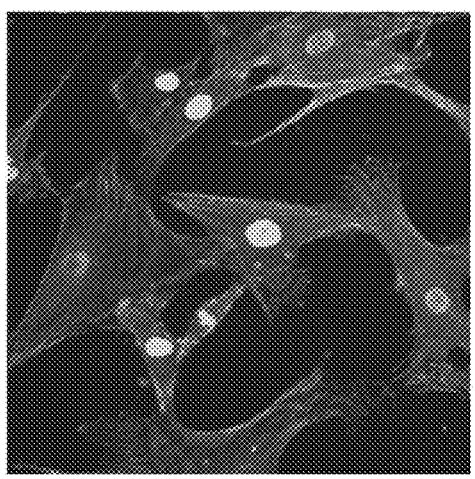
FIG. 36B is a photograph enlarged 40-fold.
Figure 37A:
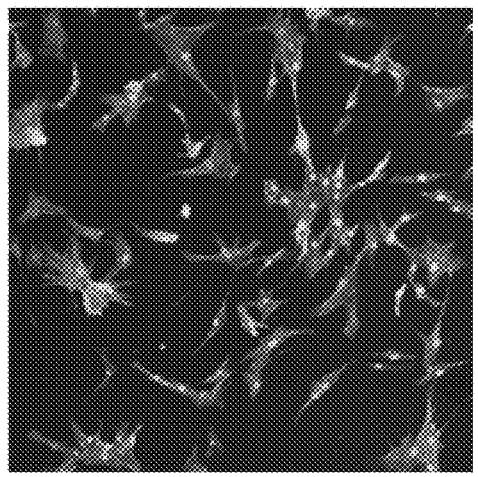
FIG. 37A is a photograph enlarged 10-fold.
Figure 37B:
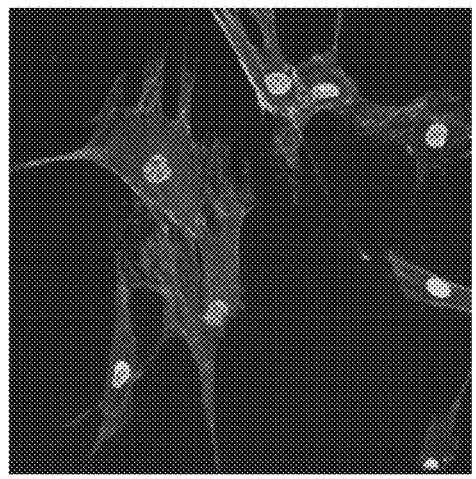
FIG. 37B is a photograph enlarged 40-fold.
Figure 38A:
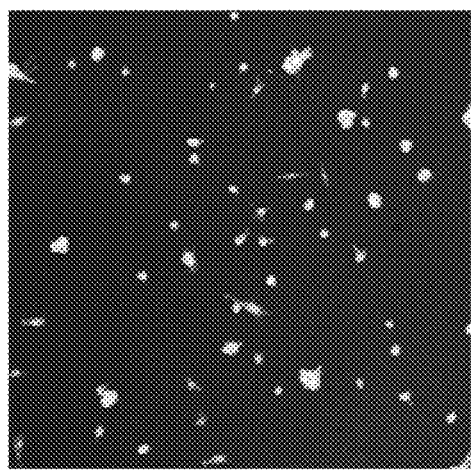
FIG. 38A is a photograph enlarged 10-fold.
Figure 38B:
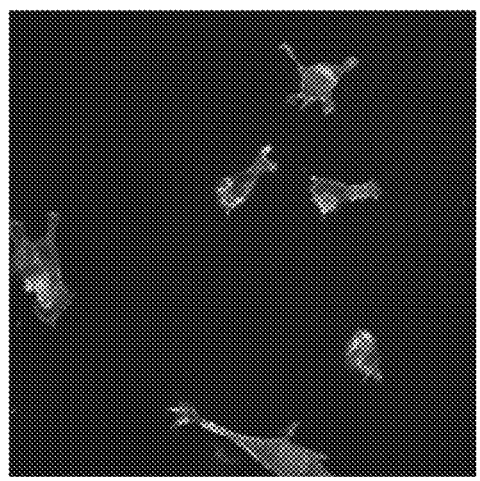
FIG. 38B is a photograph enlarged 40-fold.

Further, MTT assay results in Experiment 52 are shown in FIG. 34. When a bone marrow fluid was cultured, proliferation was not observed with the control, but remarkable proliferation was observed with SAMs (A6) to (A9).

All of the results of Experiments 1 to 4 for human bone marrow mesenchymal stem cells, the results of Experiments 21, 22 for human synovial membrane-derived mesenchymal stem cells, and the results of Experiment 23 for human dental pulp mesenchymal stem cells show similar tendency, and cell proliferation is recognized with SAMs (A6) to (A8). Consequently, with respect to the SAM composition, if hydroxyl group:carboxyl group is at a content ratio from 100:0 to 60:40, the same can be applied to adhesion and proliferation of human mesenchymal stem cells derived from other tissues, such as fat, umbilical cord, placenta, amnion, and periosteum.

(Experiments 61 to 67)

Next, adhesion and extensibility of human bone marrow mesenchymal stem cells (h-BM MSC) on to a culture dish surface was tested.

Human bone marrow mesenchymal stem cells having been cultured in advance were dispersed in STK2, inoculated in a 16-mm culture dish at a density of 4000 cells/well and cultured. Further, as a Reference Example culture was conducted the same as above with a combination of a confocal glass dish and DMEM+10% FBS or STK2. Combinations of culture media, and culture dishes used are shown in Table 9.

TABLE 9

| Exp. | Cells | Media | Culture dish |
|---|---|---|---|
| 61 | h-BM MSC | STK2 | SAM(A1) |
| 62 | h-BM MSC | STK2 | SAM(A6) |
| 63 | h-BM MSC | STK2 | SAM(A8) |
| 64 | h-BM MSC | STK2 | SAM(A11) |
| 65 | h-BM MSC | STK2 | SAM(A16) |
| 66 | h-BM MSC | DMEM + 10% FBS | Confocal glass dish |
| 67 | h-BM MSC | STK2 | Confocal glass dish |

A primary antibody and a secondary antibody were added and stained at 3 hours and 24 hours after the initiation of cultures respectively, and adhesion, extension and the like of human bone marrow mesenchymal stem cells on to a culture dish were evaluated by observation with a confocal laser scanning microscope (FV-1000D, by Olympus Corporation). The used primary antibody was Actin Cytoskeleton/Focal Adhesion Staining Kit (by Merck Millipore), and the used secondary antibody was Goat Anti-Mouse IgG (H+L) Fluorescein Conjugated (by Takara Bio Inc.).

Photographs of SAMs (A1), (A6), (A8), and (A11) are shown in FIG. 35 to FIG. 38. As the results of observation, existence or nonexistence of filopodia, lamellipodia, adhesion plaque, and stress fiber, as well as evaluations of size and shape of cells are shown in Table 10. Evaluations were conducted according to the following indices.

d: Detached or non-adherent cells
S: Small cells
L: Large cells
R: Rolled up and not extended shape
F: Flattened and extended shape
−: Nonexistent
±: Unable to judge existence or nonexistence
+: Existent
++: Many are existent

TABLE 10

| | Exp. 61 | | Exp. 62 | | Exp. 63 | | Exp. 64 | | Exp. 65 | | Exp. 66 | Exp. 67 |
|---|---|---|---|---|---|---|---|---|---|---|---|---|
| | hours | | | | | | | | | | | |
| | 3 | 24 | 3 | 24 | 3 | 24 | 3 | 24 | 3 | 24 | 24 | 24 |
| Filopodia | − | − | ± | ++ | + | ++ | − | − | − | d | ++ | d |
| Lamellipodia | ± | + | + | + | + | ++ | − | ± | − | d | ± | d |
| Adhesion plaque | − | − | + | ++ | ± | + | − | ± | − | d | ± | d |
| Stress fiber | − | ± | + | ++ | + | ++ | ± | ± | − | d | ++ | d |
| Cell size | S | S | S | L | L | L | S | S | S | d | L | d |
| Cell shape | R | R | RF | F | F | F | R | RF | R | d | F | d | d: detached and floating cells  S: small  L: large  R: round  F: flat and elongated With respect to a confocal glass dish, in the case of a serum-containing FBS culture medium (Experiment 66), since it contained an adhesion factor, existence of filopodia, and the like was observed, and the cells were enlarged by extension, but in the case of STK2 (Experiment 67), which was a serum-free culture medium, the cells did not adhere to a glass dish and filopodia or the like was absent, and extension or the like of cells was not recognized On the other hand, with SAMs (A6) and (A8) in Experiments 62 and 63, even with STK2, which is a serum-free culture medium not containing an adhesion factor, there exist many filopodia and cells extend to larger sizes. The cells interact with SAMs (A6) and (A8) actively, and therefore it is clear that the cells adhere well to an SAM surface and extension is promoted, so as to promote also cell proliferation.

(Experiment 71)

Next, using SAM (A8), differentiation of human bone marrow mesenchymal stem cells (h-BM MSC) to chondrocytes, adipocytes and osteocytes was tested.

Human bone marrow mesenchymal stem cells having been cultured in advance were recovered, then inoculated in a 16 mm-culture dish at a density of 4000 cells/well, and cultured. STK2 was used as a culture medium.

After the human bone marrow mesenchymal stem cells were proliferated to confluence, the culture medium was exchanged respectively with STK2, an adipose differentiation inducing culture medium, and STK3, and the cells were further cultured so as to differentiate the same to chondrocytes, adipocytes and osteocytes. As an adipose differentiation inducing culture medium, DMEM added with 1% Antibiotic-Antimycotic, 10% FBS, 2 mM L-glutamine, $10^{-6}$M Dex, 0.2 mM indomethacin (by Wako Pure Chemical Industries, Ltd.), 0.01 mg/mL insulin (by Wako Pure Chemical Industries, Ltd.), and 0.5 mM 3-isobutyl-1-methylxanthine (by Wako Pure Chemical Industries, Ltd.) was used. For each case, as a Reference Example an ordinary culture dish (Control) was used instead of SAM (A8) and the cells were cultured as above. In each experiment, 3 samples were tested.

(Verification of Differentiation to Chondrocytes)

After exchanging the culture medium with STK2, the culture was observed under a microscope over time to see the adhesion condition of cells to a culture dish. Further, toluidine blue staining was carried out to verify if the cells were differentiated to chondrocytes.

Figure 39:
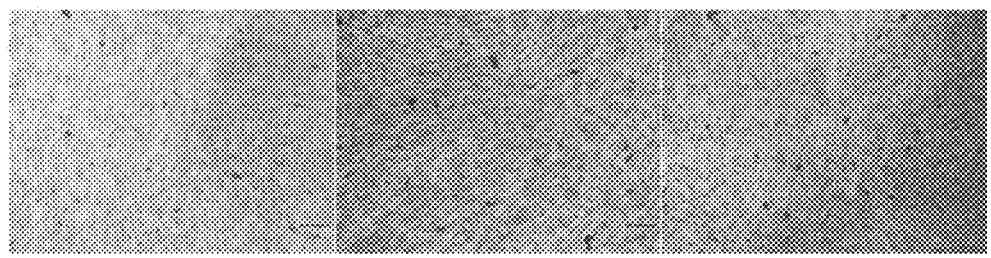
FIG. 39 is photographs of cells cultured in an ordinary culture dish and stained by toluidine blue.
Figure 40:
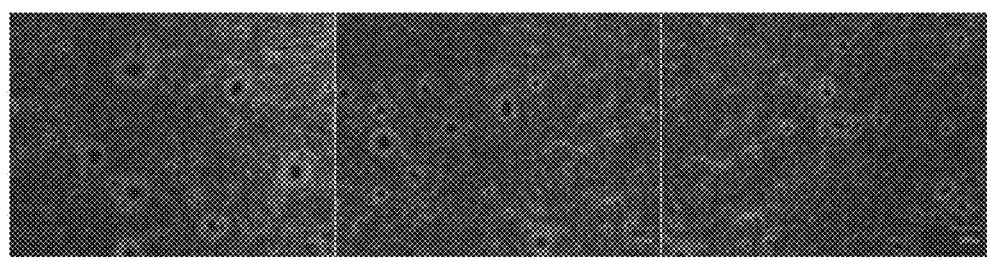
FIG. 40 is photographs of cells cultured with SAM (A8) and stained by toluidine blue.

In FIG. 39 photographs of the cells cultured in an ordinary culture dish and stained are shown, and in FIG. 40 photographs of the cells cultured with SAM (A8) and stained are shown, respectively. Further, in Table 11 the adhesion condition and the amount of the cells stained by toluidine blue staining are shown.

TABLE 11

|  | Control | | SAM(A8) | |
| --- | --- | --- | --- | --- |
|  | Adhesion condition | Toluidine blue staining | Adhesion condition | Toluidine blue staining |
| Day 0 | Adhered | ND | Adhered | ND |
| Day 5 | Adhered | ND | Adhered | ND |
| Day 6 | Adhered | ± | Adhered | ND |
| Day 18 | Detached | ND | Adhered | ND |
| Day 28 | Detached | ND | Adhered | ND |
| Day 29 | Strip | + | Adhered | +++ |

ND: not determined

With an ordinary culture dish, the cells detached from the culture dish 6 days after culture medium exchange. On the other hand, with SAM (A8) the cells maintained the condition adhered to a culture dish. Accordingly, the toluidine blue staining was conducted for SAM (A8) 29 days after the culture medium exchange, but for an ordinary culture dish 6 days after the culture medium exchange, because the cells detached from the culture dish on day 6. As the result of the toluidine blue staining, in the case of SAM (A8) many of the cells were stained indicating differentiation to chondrocytes occurred.

Figure 41:
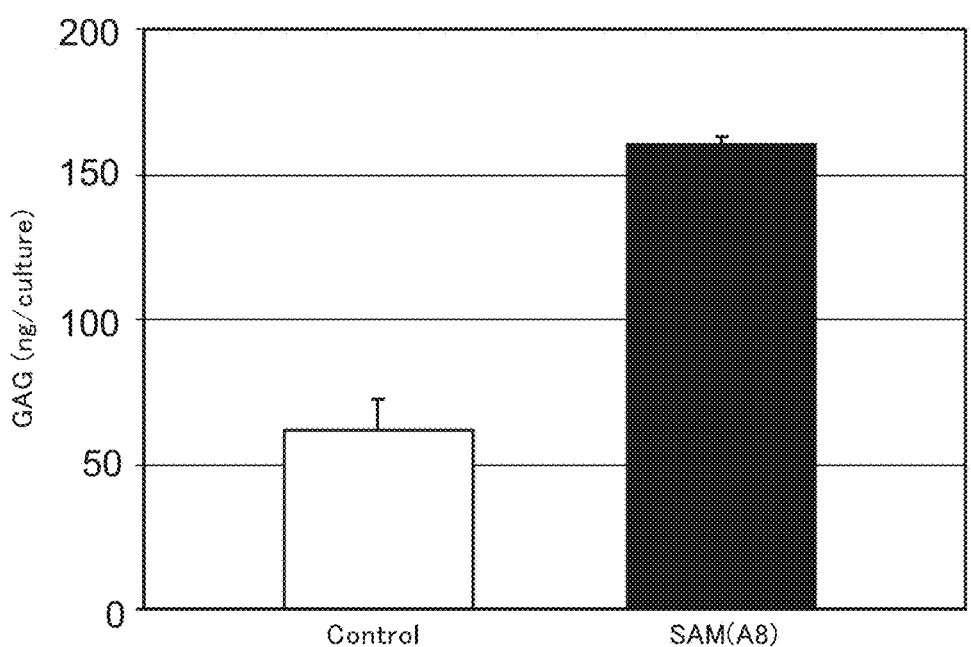
FIG. 41 is a graph showing the measurement results of GAG production amounts.

Further, it was tested whether differentiation to chondrocytes was promoted by measuring the production amount of glycosaminoglycan (GAG), which is produced when cartilage is formed. The results are shown in FIG. 41. In this regard, for both SAM (A8) and an ordinary culture dish, the GAG production amount per each culture dish was measured 28 days after the culture medium exchange.

With an ordinary culture dish GAG was approx. 60 ng/culture, and with SAM (A8) it was approx. 160 ng/culture, namely GAG was produced approx. 3-fold the case with an ordinary culture dish.

From the above results it became clear that, when human bone marrow mesenchymal stem cells were cultured with SAM (A8), differentiation to chondrocytes was promoted.

(Verification of Differentiation to Adipocytes)

Figure 42:
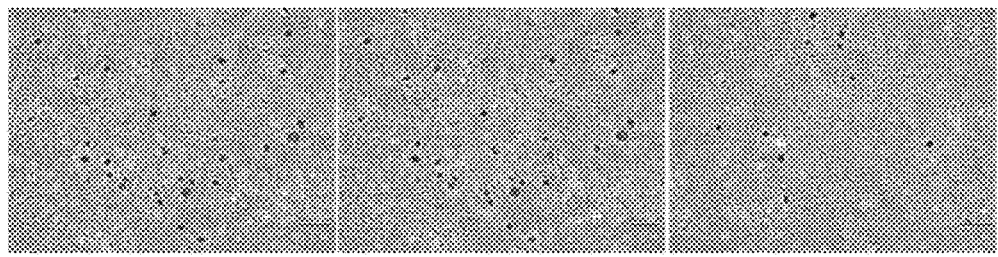
FIG. 42 is photographs of cells cultured in an ordinary culture dish and stained by Oil Red O.
Figure 43:
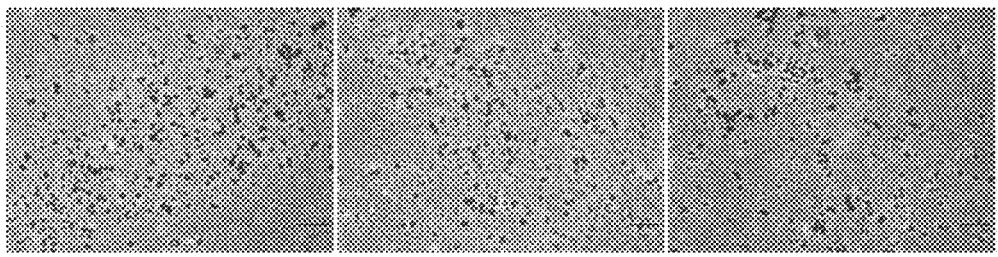
FIG. 43 is photographs of cells cultured with SAM (A8) and stained by Oil Red O.

After exchange with an adipose differentiation inducing culture medium, the culture was observed with a confocal laser scanning microscope to see the adhesion condition of the cells to a culture dish, and it was verified by oil red 0 staining whether differentiation to chondrocytes occurred. In FIG. 42 photographs of the cells cultured in an ordinary culture dish and stained are shown, and in FIG. 43 photographs of the cells cultured with SAM (A8) and stained are shown, respectively. Further, in Table 12 the amounts of the stained cells determined by visual observation are shown.

TABLE 12

|  | Control | SAM(A8) |
| --- | --- | --- |
| Day 1 | − | ND |
| Day 21 | + | +++ |

ND: not determined

It is clear that more cells are stained in the case of a culture with SAM (A8) compared to the case of a culture with an ordinary culture dish.

Figure 44:
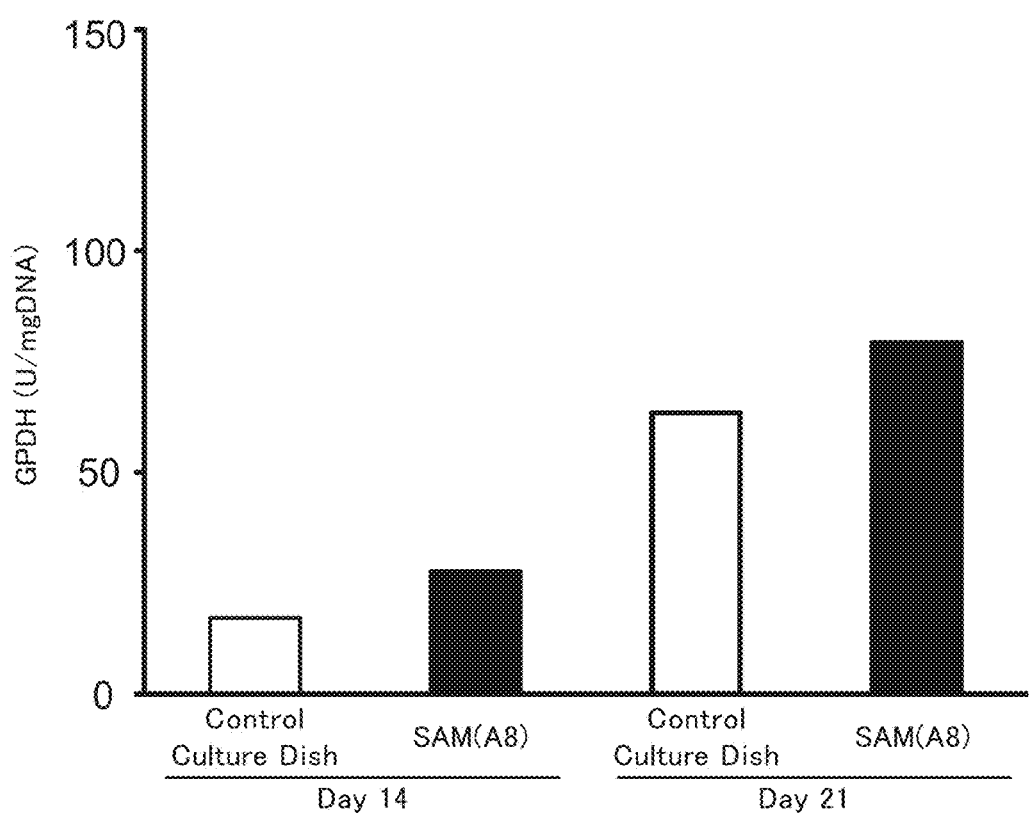
FIG. 44 is a graph showing the measurement results of GPDH amounts.

Further, the amount of GPDH (Glycerol 3-phosphate dehydrogenase) expressed by an adipocyte was measured. The results are shown in FIG. 44. It is obvious that the amount of GPDH for SAM (A8) is larger than for an ordinary culture dish. From the above results, it was known that human bone marrow mesenchymal stem cells were differentiated to adipocytes.

(Verification of Differentiation to Osteocytes)

After exchange with STK3, the activity of ALP (alkaline phosphatase), which is expressed in an osteocyte, was measured. In the present experiment a combination of an ordinary culture dish and STK3 as a Reference Example, as well as a combination of an ordinary culture dish and DMEM+10% FBS as another Reference Example (Negative Control) were also tested.

The measurement results of ALP activity are shown in FIG. 45. It is obvious that the ALP activity with SAM (A8) is higher than with an ordinary culture dish. From the results, it was known that human bone marrow mesenchymal stem cells were differentiated to osteocytes.

Meanwhile, cell differentiation can take place, when stem cells adhere to an incubator or the like and proliferate, and an appropriate differentiation-inducing culture medium is used. Therefore, SAMs (A6) to (A10), which exhibited good adhesion and proliferation of human bone marrow mesenchymal stem cells in Experiments 1 to 4, namely incubators containing hydroxyl group:carboxyl group at a content ratio from 100:0 to 20:80 on a surface are able to differentiate human bone marrow mesenchymal stem cells as in Experiment 71. In other words, if human bone marrow mesenchymal stem cells are cultured using a cartilage differentiation-inducing culture medium, the cells can be differentiated to chondrocytes. Further, by using an osteogenesis inducing culture medium, human bone marrow mesenchymal stem cells can be differentiated to osteocytes. Further, by using an adipose differentiation inducing culture medium, human bone marrow mesenchymal stem cells can be differentiated to adipocytes. In this regard, as for a cartilage differentiation-inducing culture medium and an osteogenesis inducing culture medium, even a serum-free culture medium can differentiate cells. Examples of a serum-free cartilage differentiation-inducing culture medium and osteogenesis inducing culture medium respectively include, but not limited to, STK2 and STK3 described above. And in the case where cells are differentiated using an incubator according to the present invention and a differentiation-inducing culture medium, more cells are differentiated than the case where an ordinary culture dish is used, indicating that a culturing method using an incubator according to the present invention is superior not only in cell proliferation but also in cell differentiation.

Many embodiments and variations of the present invention are possible without departing from the spirit and scope of the present invention. The above described embodiments are only for illustrating the present invention, and in no way limit the scope of the invention.

The current application is based on Japanese Patent Application No. 2011-084119 filed on 5 Apr. 2011. The entire contents including description, claims, and drawings of Japanese Patent Application No. 2011-084119 are incorporated herein by reference.

INDUSTRIAL APPLICABILITY

With respect to an animal cell culture kit according to the present invention, adhesion and proliferation of specific animal cells can be promoted even with a serum-free culture medium not containing an adhesion factor, and therefore is useful for research and development of regenerative medicine or a biopharmaceutical.

The invention claimed is:

1. An animal cell culture kit comprising:
an incubator comprising a self-assembled monolayer formed of alkanes and a serum-free culture medium;
wherein the alkanes consist of a mixture of:
1) a compound consisting of formula (I): (surface active group)-(linear alkyl chain)—hydroxyl, and
2) a compound consisting of formula (II): (surface active group)-(linear alkyl chain)—carboxyl,
wherein the surface active groups bind to the incubator or a substrate placed on the incubator,
wherein the alkanes are bound together by van der Waals forces between the linear alkyl chains such that the hydroxyl groups and the carboxyl groups are exposed at a predetermined content percent ratio, and
wherein the content percent ratio of the hydroxyl groups and the carboxyl groups is from 60:40 to 20:80.

2. The animal cell culture kit according to claim 1, further comprising a primary rat mesenchymal stem cell in a heterogeneous cell population.

3. The animal cell culture kit according to claim 1, wherein the number of carbon atoms in the linear alkyl chain is from 5 to 20.

* * * * *